(12) United States Patent
Braddock-Wilking et al.

(10) Patent No.: US 10,294,252 B2
(45) Date of Patent: May 21, 2019

(54) CYCLIC GERMANIUM COMPOUNDS AND APPLICATIONS THEREOF

(71) Applicant: The Curators Of The University Of Missouri, Columbia, MO (US)

(72) Inventors: Janet Braddock-Wilking, St. Louis, MO (US); Teresa Lynn Bandrowsky, St. Peters, MO (US); James Bryan Carroll, II, St. Louis, MO (US)

(73) Assignee: The Curators of the University of Missouri, Columbia, MO (US)

( * ) Notice: Subject to any disclaimer, the term of this patent is extended or adjusted under 35 U.S.C. 154(b) by 321 days.

(21) Appl. No.: 14/406,777

(22) PCT Filed: Jun. 11, 2013

(86) PCT No.: PCT/US2013/045201
§ 371 (c)(1),
(2) Date: Dec. 10, 2014

(87) PCT Pub. No.: WO2013/188421
PCT Pub. Date: Dec. 19, 2013

(65) Prior Publication Data
US 2015/0166581 A1 Jun. 18, 2015

Related U.S. Application Data

(60) Provisional application No. 61/689,723, filed on Jun. 11, 2012, provisional application No. 61/690,456, filed on Jun. 26, 2012.

(51) Int. Cl.
C07F 7/00 (2006.01)
C07F 7/30 (2006.01)
(Continued)

(52) U.S. Cl.
CPC ............... C07F 7/30 (2013.01); C09K 11/06 (2013.01); G01N 30/90 (2013.01);
(Continued)

(58) Field of Classification Search
CPC ........................................................ C07F 7/30
(Continued)

(56) References Cited

U.S. PATENT DOCUMENTS 3,912,655 A 10/1975 Shukla et al.
4,616,023 A 10/1986 Remy et al.
(Continued)

FOREIGN PATENT DOCUMENTS

JP 59130814 A 7/1984
WO 2006041263 A1 4/2006

OTHER PUBLICATIONS

Charles M. Gordon and Conor Long "The photochemistry of organometallic compounds of germanium, tin and lead" PATAI's Chemistry of Functional Groups in 2009 by John Wiley & Sons, Ltd.*

(Continued)

Primary Examiner — Lyle Alexander
Assistant Examiner — Emily R. Berkeley
(74) Attorney, Agent, or Firm — Armstrong Teasdale LLP

(57) ABSTRACT

The present disclosure provides a new series of compounds exhibiting high fluorescence quantum yields in the solid state. In one embodiment, the compounds include a series of 2,3,4,5-tetraphenylgermoles with the same or different 1,1-substituents. In another embodiment, substituted germafluorenes, germa-fluoresceins/rhodamines, and germapins are described. These germanium heterocycles possess ideal photophysical and thermostability properties, which makes them excellent candidates for chemical or biological sensors, host materials for electroluminescent devices and solar (Continued)

cells, and emissive and for electron-transport layer components in organic light emitting diode devices.

8 Claims, 15 Drawing Sheets

(51) Int. Cl.
*G01N 30/90* (2006.01)
*C09K 11/06* (2006.01)

(52) U.S. Cl.
CPC .......... *C09K 2211/1007* (2013.01); *C09K 2211/1014* (2013.01); *C09K 2211/1029* (2013.01); *C09K 2211/1051* (2013.01); *C09K 2211/1092* (2013.01); *C09K 2211/1096* (2013.01); *Y10T 436/202499* (2015.01)

(58) Field of Classification Search
USPC .......................................................... 436/130
See application file for complete search history.

(56) References Cited

U.S. PATENT DOCUMENTS

| | | |
|---|---|---|
| 7,482,168 B2 | 1/2009 | Sailor et al. |
| 7,943,775 B2 | 5/2011 | Li et al. |

OTHER PUBLICATIONS

Teresa L. Bandrowsky, James B. Carroll, and Janet Braddock-Wilking "Synthesis, Characterization, and Crystal Structures of 1,1-Disubstituted-2,3,4,5-tetraphenylgermoles That Exhibit Aggregation-Induced Emission" Organometallics 2011, 30, 3559-3569.*
Jerome L. Mullin, Henry J. Tracy, James R. Ford, Scott R. Keenan, and Fred Fridman "Characteristics of Aggregation Induced Emission in 1,1-Dimethyl-2,3,4,5-tetraphenyl and 1,1,2,3,4,5-Hexaphenyl Siloles and Germoles" Journal of Inorganic and Organometallic Polymers and Materials, vol. 17, No. 1, Mar. 2007.*
Teresa L. Bandrowsky, James B. Carroll, and Janet Braddock-Wilking "Synthesis, Characterization, and Crystal Structures of 1,1-Disubstituted-2,3,4,5-tetraphenylgermoles That Exhibit Aggregation-Induced Emission" Organometallics 2011, 30, 3559-3569 (Year: 2011).*
Bandrowsky et al. Organometallics 2011, 30, 3559-3569 (Year: 2011).*
International Search Report and Written Opinion from International Patent Application No. PCT/US13/45201, dated Nov. 12, 2013.
Tsangaris, JM "Synthesis of M(IV) Organometallic Compounds, where M=Ge, Sn, Pb" The Chemistry of Organic Germanium, Tin and Lead Compounds, vol. 1, John Wiley & Sons, Ltd., 1995, ISBN: 0-471-94207-3; compound 9, scheme 9 on p. 461.
Brooks, EH et al. "790. Diphenylphosphino-organogermanes" Journal of the Chemical Society, Issue 0, 1965, [Retrieved from the internet on Oct. 28, 2013] <URL: http://pubs.rsc.org/en/Content/ArticleLanding/1965/JR/JR9650004283#!divAbstract>; abstract.
Gordon, CM et al. "The Photochemistry of Organometallic Compounds of Germanium, Tin and Lead" The Chemistry of Organic Germanium, Tin and Lead Compounds, vol. 1. John Wiley & Sons, Ltd., 1995, ISBN: 0-471-94207-3; compound 32, scheme 10, p. 739.
Dong et al., "Vapochromism and Crystallization-Enhanced Emission of 1,1-Disubstituted 2,3,4,5-Tetraphenylsiloles" J. Inorg. Organomet. Polym. 2007, 17, 673-678.
Mullin et al., "Characteristics of Aggregation Induced Emission in 1,1-Dimethyl,2,3,4,5-tetraphenyl and 1,1,2,3,4,5-Hexaphenyl Siloles and Germoles," Journal of Inorganic & Organometallic Polymers and Materials, 2007, vol. 17, No. 1, pp. 201-213.
Chen et al., "Synthesis, Light Emission, Nanoaggregation, and Restricted Intramolecular Rotation of 1,1-Substituted 2,3,4,5-Tetraphenylsiloles" Chem. Mater., 2003, 15(7), pp. 1535-1546.
Tracy et al., "Enhanced Photoluminescence from Group 14 Metalloles in Aggregated and Solid Solutions," Inorg. Chem., 2005, 44, pp. 2003-2011.
Huc et al., "Synthesis of functionalized mono-, di-, tri-, and tetraphosphines: Attempted Application to Prepare Hyperbranched Polymers and Dendrimers Built with Phosphines at Each Branching Point", Synthesis, 2000, No. 5, pp. 726-730.
Curtis et al., "Synthesis and Reactions of Some Functionally Substituted Sila- and Germacyclopentadienes." Journal of American Chemical Society, 1969, 91(22), pp. 6011-6018.

\* cited by examiner

Scheme 4

CYCLIC GERMANIUM COMPOUNDS AND APPLICATIONS THEREOF

CROSS-REFERENCE TO RELATED APPLICATIONS

This application claims priority to International Application Number PCT/US2013/045201, filed on Jun. 11, 2013, U.S. Provisional Patent Application No. 61/690,456, filed on Jun. 26, 2012, and U.S. Provisional Patent Application No. 61/689,723, filed on Jun. 11, 2012, the disclosures of which are hereby expressly incorporated by reference in their entireties.

GRANT STATEMENT

This invention was made with Government support under Grant No. CHE-0719380 awarded by the National Science Foundation. The Government has certain rights in the invention.

FIELD OF THE DISCLOSURE

The present disclosure relates to compounds for use as luminescent materials and, most specifically, as luminescent materials that exhibit high fluorescence quantum yields in the solid state. The compounds are ideal candidates for a variety of applications, including for use as electron-transporting or emissive layers in semiconducting and electronic, devices and as chemical and biological sensors. In one particular embodiment, the compounds are used as chemosensors for the detection of volatile organic compounds (VOCs) such as acetone.

BACKGROUND OF DISCLOSURE

For the past few decades, the development of efficient luminescent materials, having desirable optoelectronic properties, has been a topic of great interest. The development of efficient luminescent materials, however, has been hindered by problems associated with aggregation-caused quenching of light emission which is notorious for rendering luminophors ineffective for solid state applications, particularly those involving electroluminescent (EL) devices. In order for luminescent materials to have practical applications as electron-transporting or emissive layers as thin films in semiconducting and electronic devices, a luminophor should exhibit high fluorescence quantum yield ($\Phi_F$) in the solid state. Many organic fluorophores experience aggregation-caused quenching (ACQ) of light emission in solution as well as the solid state as a result of interactions with neighboring fluorophores which promote the formation of delocalized excitons or excimers which decay non-radiatively. As a result, low concentrations of the fluorophore molecule must be used in order to minimize contact between adjacent molecules to mitigate the ACQ effect resulting in decreased sensitivity and reliability of the fluorescent signal. A logical approach to alleviating the problems associated with ACQ would be to develop luminophors whose aggregates fluoresce more strongly than their solutions. Identification of two photoluminescence processes, aggregation-induced emission (AIE) and aggregation-induced emission enhancement (AIEE), may now allow development of highly efficient solid state fluorescence. In AIE, a non-emissive chromophore is induced to emit light by the formation of aggregates while the light emission of an AIEE molecule is significantly enhanced once aggregation occurs.

Silacyclopentadienes, or siloles (FIG. 1, M=Si), are a class of molecules that have been previously extensively developed for their potential application in organic electronics, particularly in flexible lighting and display panels. One of the qualities responsible for the intense interest in siloles is the high electron affinity that these cyclic molecules exhibit. Such large electron affinities can be attributed to a low lying LUMO which arises from $\sigma^*$-$\pi^*$ conjugation that results from the interaction between the $\pi^*$ orbital of the butadiene segment and the $\sigma^*$ orbital associated with the two exocyclic bonds on the silicon center. The large electron affinity of the siloles results in another favorable feature, high electron mobility, a desirable attribute that continues to present challenges in the design of highly efficient organic electronic devices. There are many silole derivatives that have been reported to be good electron transporters with electron mobilities that are two orders of magnitude higher than tris(8-hydroxyquinolinato)aluminum ($Alq_3$). $Alq_3$ is a commonly used electron-transport (ET) material for organic light-emitting diodes (OLEDs).

Siloles have demonstrated high photoluminescence (PL) quantum yields as both amorphous and crystalline solids which can be attributed to the unique photophysical property of aggregation-induced emission (AIE). As a result of the steric repulsions between the peripheral aryl substituents on the core ring, intramolecular rotations of the substituents are restricted causing the substituents on the silole core to assume a highly twisted conformation that persists in solution as well as the solid state. Restriction of intramolecular rotations of the peripheral substituents effectively blocks non-radiative relaxation channels and imparts non-planarity, rendering the distance between adjacent silole molecules too long for conventional $\pi$-$\pi$ stacking interactions (~3-4 Å) that typically quench luminogens in the solid and crystalline phases. This mechanism is referred to as restricted intramolecular rotation (RIR) and is the accepted cause of the AIE phenomenon. RIR so effectively deactivates the avenues that result in non-radiative emission that siloles strongly emit light in the solid and crystalline phases, such as aggregated suspensions in solvent-water mixtures.

The AIE effect has now been identified in other luminogens with similar structural features including germoles, the heavier Group 14 congener of siloles (FIG. 1, M=Ge). Although germoles emit more efficiently in solution than siloles, their solutions are still only weakly emissive. The increased efficiency in solution, however, does not diminish the significant AIE effect that is exhibited by germoles in the solid state or when aggregated in solvent-water mixtures. Germoles, like siloles, are soluble in a variety of common organic solvents, but insoluble in water.

To date, relatively little has been published on the PL of germoles, despite published evidence of the similarities between siloles and germoles. In addition to exhibiting the AIE effect, parallels between the electronic structure and photophysical properties of the two metalloles can be seen by the similarities in the UV-vis absorption and fluorescence profiles, electrochemical data, and ab initio calculations of HOMO and LUMO energy levels. Such studies indicate comparable $\sigma^*$ (Si—R) and $\sigma^*$ (Ge—R) orbitals as well low lying LUMO energy levels, suggesting that the differences in the electronic structures of germanium and silicon analogs are relatively minimal despite the slightly larger size of the germanium atom. This is in contrast to the attributes that would be gleaned from the low lying LUMO in stannoles which are diminished by significantly less efficient $\sigma^*$-$\pi^*$ conjugation that results from a greater orbital mismatch as well as elongated bond distances between the larger $5p_z$ $\sigma^*$ orbital of tin and the $2p_z\pi^*$ orbital of the carbons of the butadiene.

Therefore, there is a need to develop a series of compounds containing a germanium ring core, and in particular, germoles, exhibiting intense fluoresce quantum yields as aggregates in solution or in the solid state to be employed in light-emitting devices and luminescent sensors.

SUMMARY OF THE DISCLOSURE

The present disclosure provides a new series of luminescent compounds containing a germanium ring core. In particularly suitable embodiments, the compounds are substituted germoles, substituted germafluorenes, substituted germa-fluoresceins or germa-rhodamines or substituted germapins, exhibiting high fluorescence quantum yields in the solid state.

Accordingly, in one embodiment, the compounds are a series of 2,3,4,5-tetraphenylgermoles with same or different 1,1-substituents, which may have the formula (I)

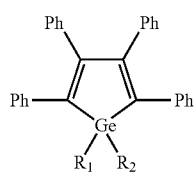
(I)

wherein $R_1$ and $R_2$ may be independently selected from optionally substituted aryl, optionally substituted heteroaryl, or optionally substituted alkynyl.

In another embodiment, the compounds are a series of substituted germafluorenes having the general formula (II)

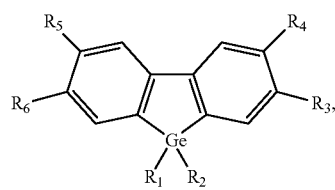
(II)

wherein $R_1$ and $R_2$ may be independently selected from the group consisting of aryl, alkyl, halide, alkynyl, and asymmetric derivatives thereof with two different groups at the Ge-center;

wherein $R_3$ and $R_6$ may be independently selected from the group consisting of Y and

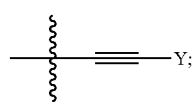

wherein $R_4$ and $R_5$ may be independently selected from the group consisting of $OCH_3$ and Y; and wherein Y is H,

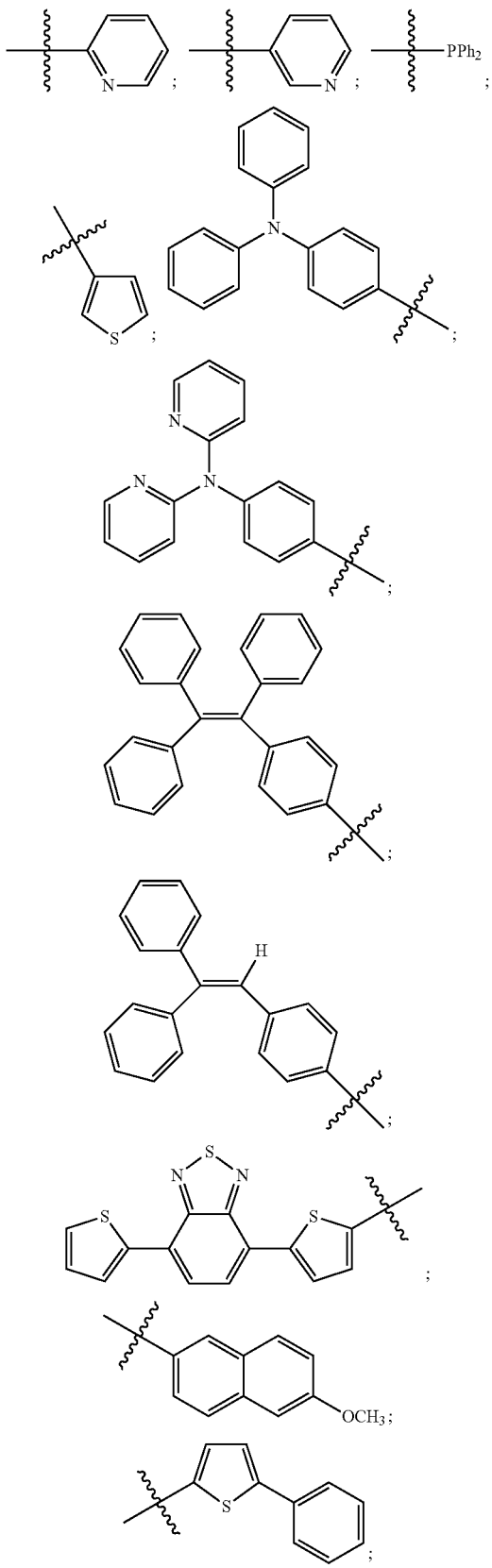

-continued

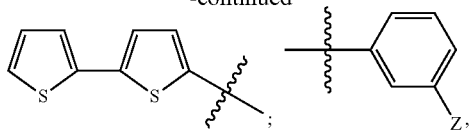

wherein Z is F, CH₃, or OCH₃;

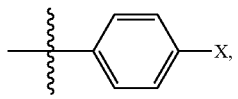

wherein X is H, CF₃, OPh, CH₃, Ph, OCH₃ or OCF₃; or

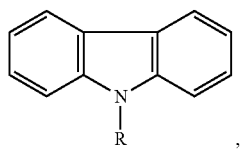

wherein R is aryl, alkenyl or alkynyl.

In yet another embodiment, the compounds are substituted germa-fluoresceins or germa-rhodamines having the general formula (III)

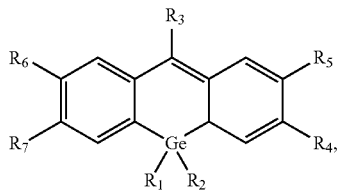
(III)

wherein $R_1$ and $R_2$ may be independently selected from the group consisting of aryl, alkyl, halide, alkynyl, and asymmetric derivatives thereof with two different groups at the Ge-center;
wherein $R_4$ and $R_7$ may be independently selected from the group consisting of =O, —OH, and OSi(CH₃)₂[(CH₃)₃] hydroxyl or carbonyl amine and ether derivatives;
wherein $R_5$ and $R_6$ are H; and
wherein $R_3$ is Y, =O, C₆H₅, p-CH₃C₆H₅, p-CH₃OC₆H₅ or

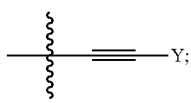

wherein Y is

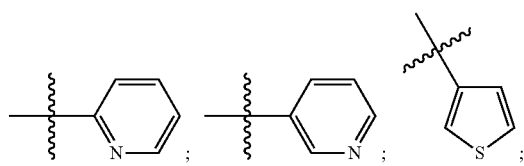

-continued

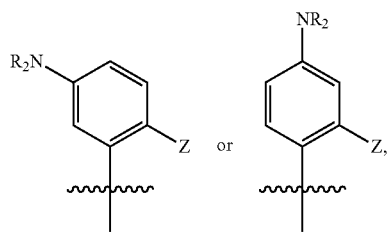

wherein Z is F, CH₃ or OCH₃;

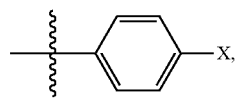

wherein X=CF₃, OPh, CH₃, Ph, OCH₃ or OCF₃;

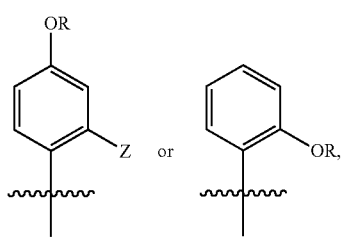

wherein NR₂=NH₂, NMe₃ or NEt₂ and Z=Me, CO₂H, C(=O)H, or CO₂Me;

wherein R is alkyl and Z=Me, CO₂H, CO₂Me; or,

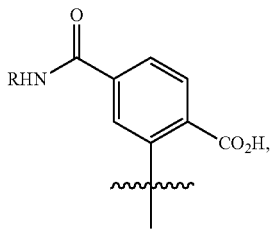

wherein R is alkyl or H.

In another embodiment, the compounds are substituted germapins having the general formula (IV)

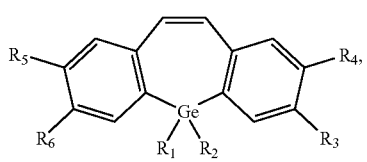

(IV)

wherein $R_1$ and $R_2$ may be independently selected from the group consisting of aryl, alkyl, halide, alkynyl, and asymmetric derivatives thereof with two different groups at the Ge-center;

wherein $R_3$ and $R_6$ may be independently selected from the group consisting of H, Cl, Ar, Y and

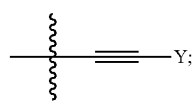

wherein $R_4$ and $R_5$ may be independently selected from the group consisting of H, aryl, I, Br, Y or

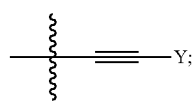

and
wherein Y is

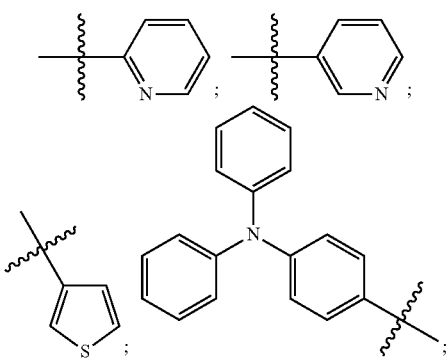

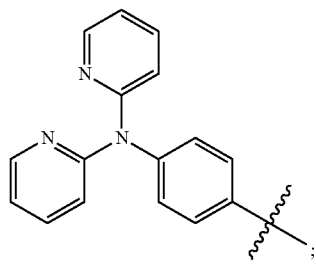

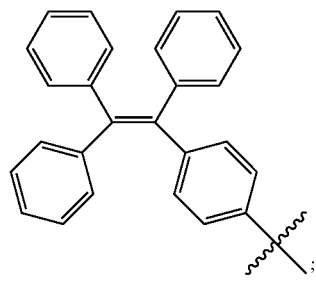

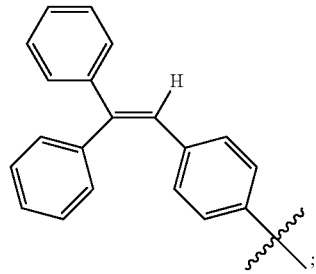

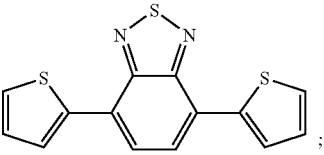

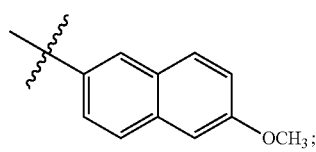

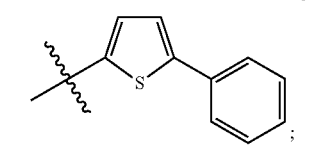

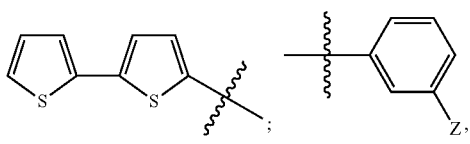

wherein Z is F, CH₃ or OCH₃;

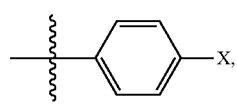

wherein X is CF$_3$, OPh, CH$_3$, Ph, OCH$_3$ or OCF$_3$; or

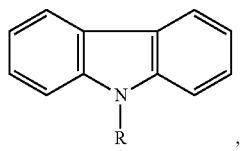

wherein R is aryl, alkenyl or alkynyl.

The compounds of the present disclosure with their ideal photophysical and thermostability properties may make them excellent candidates for chemical or biological sensors, host materials for electroluminescent devices, solar cells, and light-emitting materials in organic light emitting diode devices (OLEDs).

According to one particular embodiment of the present disclosure, germoles may be employed as coating materials on thin layer chromatography (TLC) plates for chemical or biological sensing (such as detection of organic vapor compounds).

According to another embodiment of the present disclosure, germoles germafluorenes, germa-fluoresceins/germarhodamines, and germapins may be tuned to develop blue, green, or the more rare red light-emitting materials, which may be employed as the emissive and/or electron-transport layer components in organic light emitting, diode devices (OLEDs). In another embodiment of the present disclosure, the germafluoroenes may be used as a reagent to stain/detect subcellular organelles in cell imaging applications (e.g., staining of the mitochondria).

DETAILED DESCRIPTION OF THE DISCLOSURE

The present disclosure provides several new classes of luminescent compounds containing a cyclic germanium core. Specifically, the compounds are separated into four groups: (I) germoles, (II) germafluorenes, (III) germa-rhodamines or germa-fluoresceins, and (IV) germapins with the following respective formulas

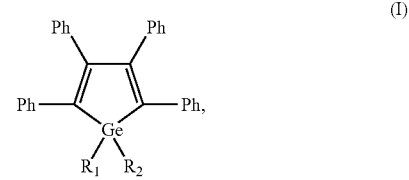

-continued

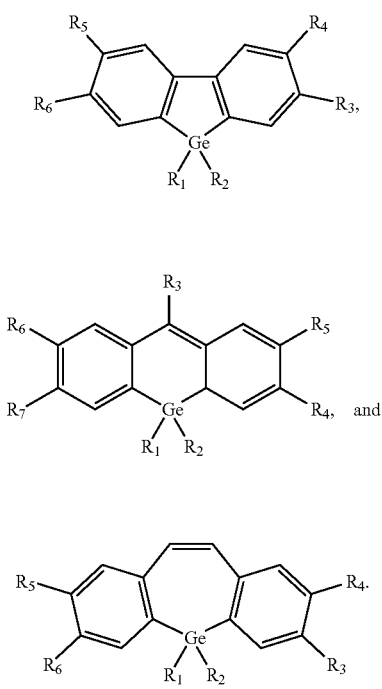

(II)

(III)

(IV)

The present disclosure also provides synthetic schemes for the inventive compounds.

Germoles

Figure 1:
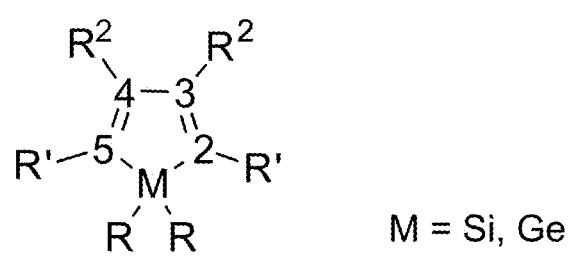
FIG. 1 is the basic metallole structure, M=Si, silole, M-Ge, germole: 2,3,4,5=C.

In one aspect, the present disclosure is directed to a new series of germoles as luminophore materials with desirable thermal and morphological properties, especially the unique photophysical property of aggregation-induced emission (AIE). The research endeavor was to devise ways to introduce substituents at the 1,1-positions (FIG. 1) that were different from the traditional phenyl or methyl groups that are typically utilized for germoles. The present disclosure is directed to two distinct classes within this series: germoles possessing the same two substituents (symmetrical) and those with different substituents (unsymmetrical) at the germanium center. The preparation of these classes is disclosed.

In one embodiment, the germoles are a series of 2,3,4,5-tetraphenylgermoles with same (symmetrical) or different (unsymmetrical) 1,1-substituents, which may have the formula (I)

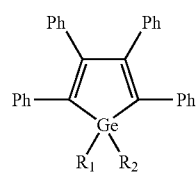

(I)

wherein $R_1$ and $R_2$ may be independently selected from optionally substituted aryl, optionally substituted heteroaryl, or optionally substituted alkynyl. According to one embodiment of the disclosure, $R_1$ and $R_2$ may be selected independently from the group consisting of

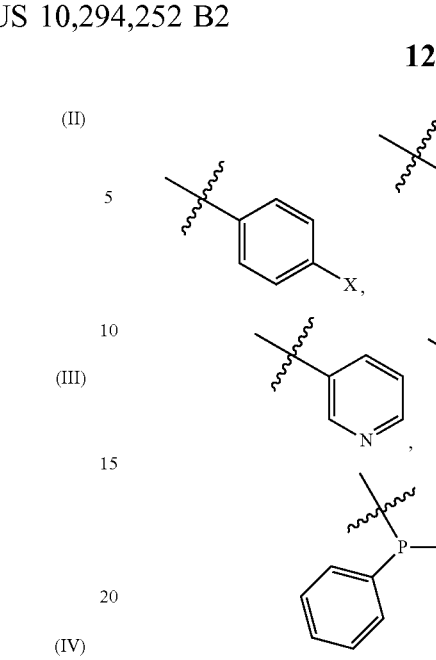

wherein X=H, $CF_3$, $OCF_3$,
$CH_3$, $OCH_3$, Ph, OPh
and derivatives thereof.

In one embodiment of the present disclosure, $R_1$ and $R_2$ are each

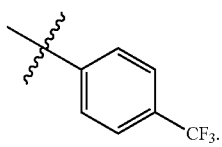

In another embodiment of the present disclosure, $R_1$ and $R_2$ are each

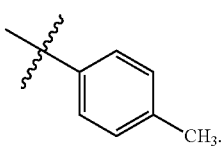

In yet another embodiment of the present disclosure, $R_1$ and $R_2$ are each

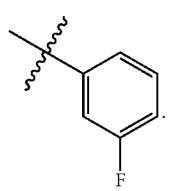

In still another embodiment of the present disclosure, $R_1$ and $R_2$ are each

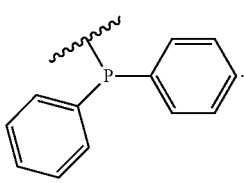 [SMILES: *P(c1ccccc1)c1ccccc1]

In still another embodiment, the aryl is optionally substituted phenyl.

As used herein, "aryl" refers to a radical of a monocyclic or polycyclic (e.g., bicyclic or tricyclic) 4n+2 aromatic ring system (e.g., having 6, 10, or 14 electrons shared in a cyclic array) having 6-14 ring carbon atoms and zero heteroatoms provided in the aromatic ring system ("C6-14 aryl"). In some embodiments, an aryl group has 6 ring carbon atoms ("C6 aryl"; e.g., phenyl). In some embodiments, an aryl group has 10 ring carbon atoms ("C10 aryl"; e.g., naphthyl such as 1-naphthyl and 2-naphthyl). In some embodiments, an aryl group has 14 ring carbon atoms ("C14 aryl"; e.g., anthracyl).

Exemplary substituents include groups that contain a heteroatom (such as nitrogen, oxygen, silicon, phosphorous, boron, sulfur, or a halogen atom), halogen (e.g., chlorine, bromine, fluorine, or iodine), a heterocycle, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers. In one embodiment, the compounds comprise "heteroaryls."

As used herein, "alkyl" refers to a radical of a straight-chain or branched saturated hydrocarbon group having from, in some embodiments, 1 to 4 carbon atoms ("C1-4 alkyl"), and in other embodiments 1 to 22 carbon atoms ("C1-22 alkyl"). In some embodiments, an alkyl group has 1 to 3 carbon atoms ("C1-3 alkyl"). In some embodiments, an alkyl group has 1 to 2 carbon atoms ("C1-2 alkyl"). In some embodiments, an alkyl group has 1 carbon atom ("C1 alkyl"). In some embodiments, an alkyl group has 2 to 4 carbon atom ("C2-4 alkyl"). In yet other embodiments, an alkyl group has 1 to 21 carbon atoms ("C1-21 alkyl"), 1 to 20 carbon atoms ("C1-20 alkyl"), 1 to 15 carbon atoms ("C1-15 alkyl"), 1 to 10 carbon atoms ("C1-10 alkyl"), etc. Examples of such alkyl groups include methyl (C1), ethyl (C2), n-propyl (C3), isopropyl (C3), n-butyl (C4), tert-butyl (C4), sec-butyl (C4), iso-butyl (C4), pentyl (C5), and the like.

As used herein, "alkenyl" or "alkene" refers to a radical of a straight-chain or branched hydrocarbon group having from, in some embodiments, 2 to 4 carbon atoms ("C2-4 alkenyl"), and in other embodiments 2 to 22 carbon atoms ("C2-22 alkenyl"), and one or more carbon-carbon double bonds. In some embodiments, an alkenyl group has 2 to 3 carbon atoms ("C2-3 alkenyl"). In some embodiments, an alkenyl group has 2 carbon atoms ("C2 alkenyl"). In yet other embodiments, an alkenyl group has 2 to 21 carbon atoms ("C2-21 alkenyl"), 2 to 20 carbon atoms ("C2-20 alkenyl"), 2 to 15 carbon atoms ("C2-15 alkenyl"), 2 to 10 carbon atoms ("C2-10 alkyl"), etc. The one or more carbon-carbon double bonds can be internal (such as in 2-butenyl) or terminal (such as in 1-butenyl). Examples of such alkenyl groups include: ethenyl (C2), 1-propenyl (C3), 2-propenyl (C3), 1-butenyl (C4), 2-butenyl (C4), butadienyl (C4), 1-pentenyl (C5), 2-pentenyl (C5), and the like.

As used herein, "alkynyl" or "alkyne" refers to a radical of a straight chain or branched hydrocarbon group having from 2 to 4 carbon atoms and one or more carbon-carbon triple bonds ("C2-10 alkynyl"). In some embodiments, an alkynyl group has 2 to 3 carbon atoms ("C2-3 alkynyl"). In some embodiments, an alkynyl group has 2 carbon atoms ("C2 alkynyl"). The one or more carbon-carbon triple bonds can be internal (such as in 2-butynyl) or terminal (such as in 1-butynyl). Examples of C2-4 alkynyl groups include, without limitation, ethynyl (C2), 1-propynyl (C3), 2-propynyl (C3), 1-butynyl (C4), 2-butynyl (C4), and the like.

Alkyl, alkenyl, alkynyl and aryl groups, as defined herein, are substituted or non-substituted, also referred to herein as "optionally substituted". In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that result in the formation of a stable compound. The present disclosure contemplates any and all such combinations in order to arrive at a stable compound. For purposes of this disclosure, heteroatoms such as nitrogen may have hydrogen substituents and or any suitable substituent as described herein which satisfy the valencies of the heteroatoms and results in the formation of a stable moiety.

Figure 2:
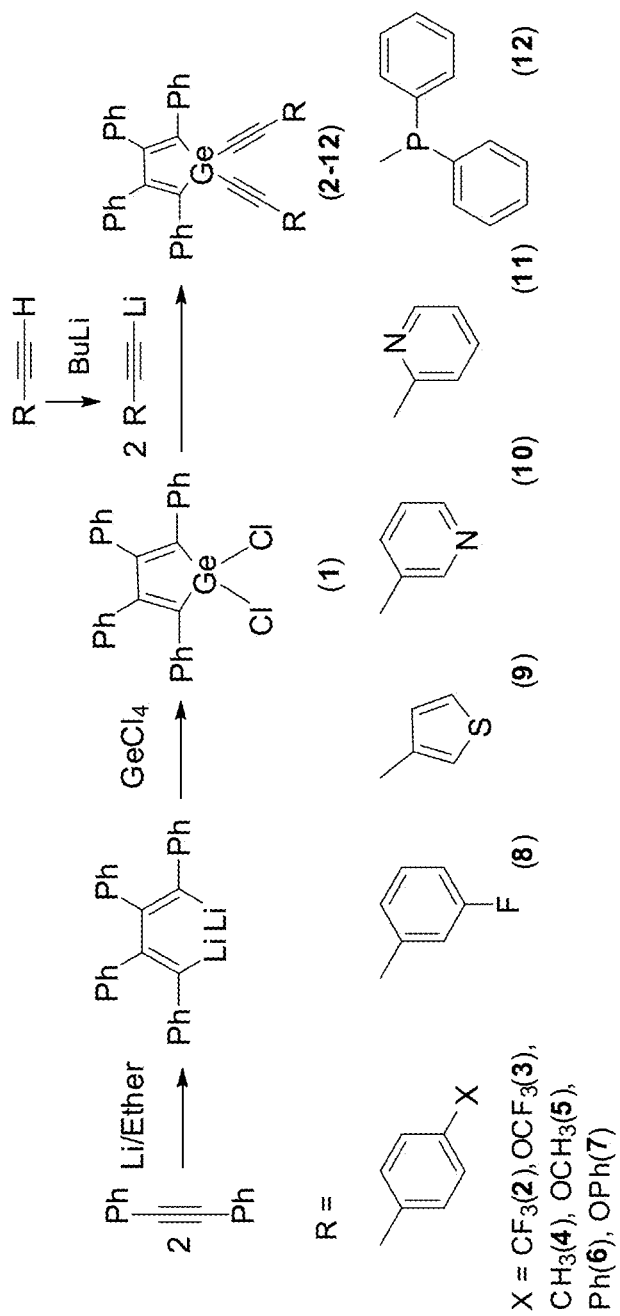
FIG. 2 illustrates the synthesis scheme for germole compounds of the present disclosure according to one embodiment of the present disclosure.
Figure 11:
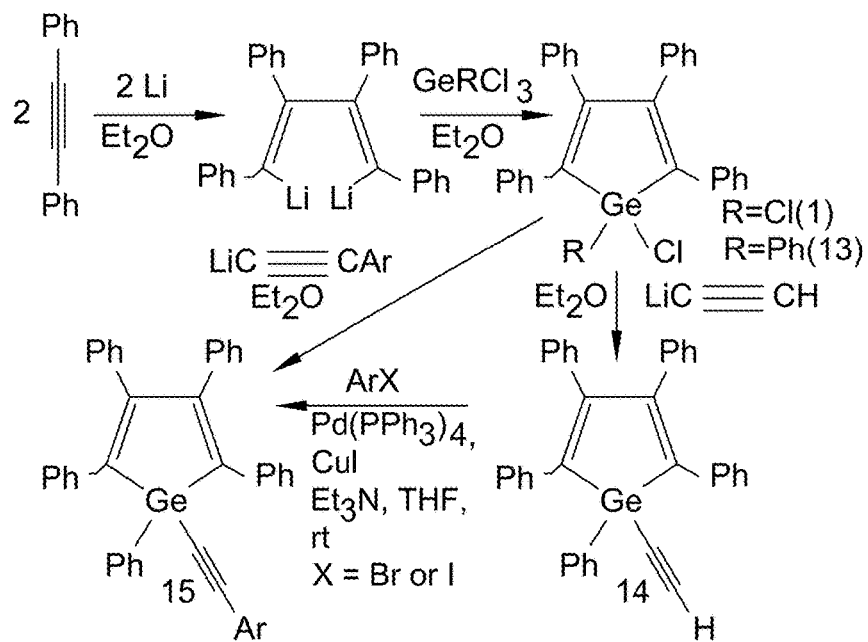
FIG. 11 illustrates an exemplary synthesis scheme for germole compounds of the present disclosure according to one embodiment of the present disclosure.
Figure 11:
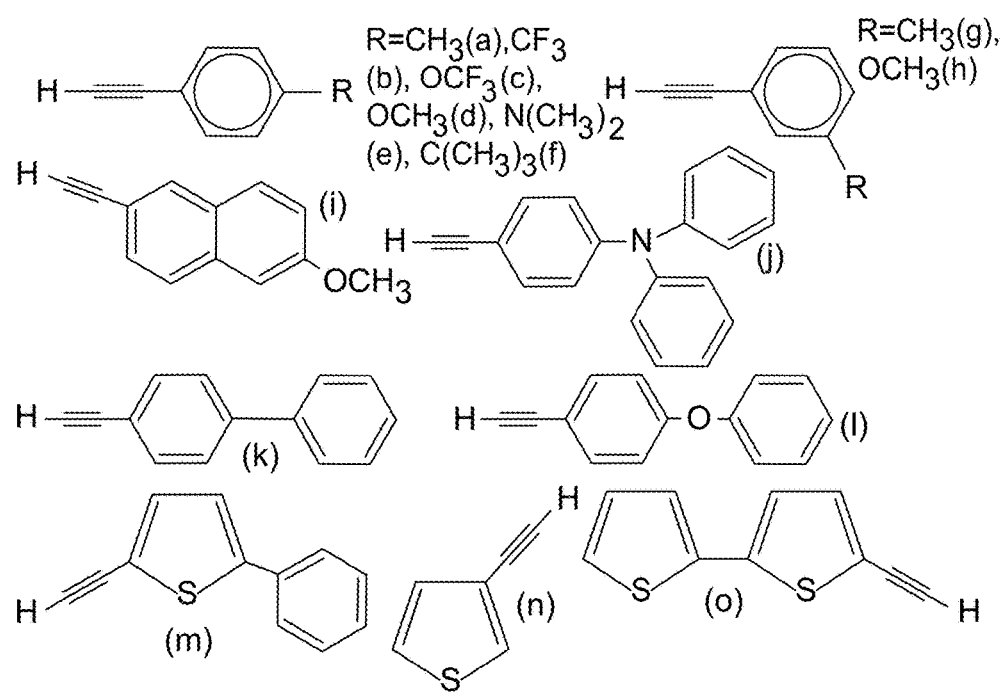

The disclosure also provides synthetic schemes for the inventive compounds. FIGS. 2 and 11 illustrates an exemplary synthesis for exemplary germole compounds. FIG. 11 also lists the possible substituting aryl (Ar) groups, which may be potential R groups for all groups of inventive compounds of the present disclosure.

Symmetrical 1,1-Disubstituted Germoles

The present disclosure is further directed to the synthesis and characterization of these germoles and their AIE effects and applications. The germoles intensely fluoresce in the blue-green region (478-488 nm) in the solid phase. The electronegativity of the 1,1-substituents exhibit a modest inductive effect on the UV-vis and fluorescence wavelength maxima. Although the germoles of the present disclosure exhibited higher quantum yields in solution than other characterized germoles, their room temperature solutions are only weakly emissive. In comparison to siloles, the germoles of the present disclosure are ca. 3× more emissive in solution, resulting in a smaller enhancement of luminescence when aggregated. The smaller enhancement between the luminescence of the molecularly dissolved and aggregated solutions of the inventive germoles should not discourage exploiting the AIE effect in these systems. The AIE effect in the germoles of the present disclosure is quite pronounced and may be employed in many potential applications as efficient emitters in aqueous media, coating materials on TLC for chemical or biological sensing, and emissive and/or electron-transport layer components in organic light emitting diode devices (OLEDs).

Thus, in one embodiment, the disclosure is directed to a TLC plate for detection of organic vapor compounds comprising a coating layer comprising a compound having the formula (I)

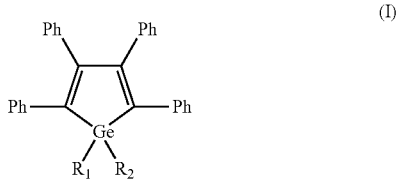

(I)

wherein $R_1$ and $R_2$ may be independently selected from optionally substituted aryl, optionally substituted heteroaryl, or optionally substituted alkynyl. According to one embodiment of the disclosure. $R_1$ and $R_2$ may be selected independently from the group consisting of

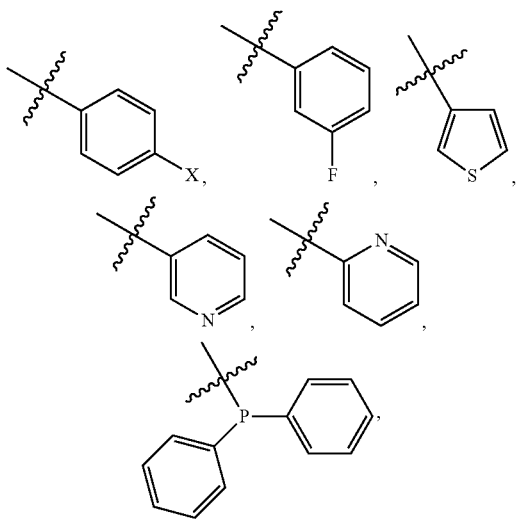

wherein X=H, $CF_3$, $OCF_3$,
$CH_3$, $OCH_3$, Ph, OPh
and derivatives thereof.

In the TLC plate embodiments. $R_1$ and $R_2$ may each be

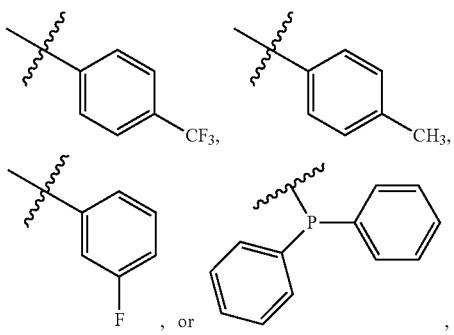

Referring to FIG. 2, which illustrates an exemplary synthetic scheme for the symmetrical 1,1-disubstituted germoles of the present disclosure, 1,1-Dichloro-2,3,4,5-tetraphenylgermole 1 may be prepared by a ring-closure reaction of 1,4-dilithio-1,2,3,4-tetraphenyl-1,3-butadiene with germanium tetrachloride according to the procedure reported by Curtis et al. Am. Chem. Soc. 1969, 91, 6011-6018, which is hereby incorporated by reference to the extent it is consistent herewith. In contrast to the synthesis of 1,1-dichloro-2,3,4, 5-tetraphenylsilole, the germole 1 can be prepared without difficulty in high yield (70-95%). The germole 1 is virtually insoluble in $Et_2O$ and precipitates in relatively high purity from the reaction mixture whereas the related silole requires a low temperature reaction for the addition step of $SiC_{14}$. Isolated 1 can be converted to new 1,1-disubstituted germoles (2 through 12) by addition of various alkynyllithium reagents that are generated from commercially available terminal acetylenes and "BuLi. Due to the relatively short lifetime of the lithiated alkyne species, the yields of germoles 2 through 12 are lower and varied from 44-70%. The diphenylphosphine-substituted precursor is not commercially available and may be prepared according to a known procedure, such as disclosed in Huc et al. Synthesis 2000, 726-730, which is hereby incorporated by reference to the extent it is consistent herewith.

All of these germoles exhibit the unusual phenomenon of Aggregation-Induced Emission (AIE) in the solid state. Germoles 2, 8, and 1,1-diethynyl were tested as potential chemosensors for the detection of volatile organic compounds (VOCs) such as acetone. Thin films of the germoles on TLC silica gel plates showed strong emission but upon exposure to acetone the emission is rapidly quenched but after evaporation of the solvent strong emission resumes.

The germoles of the present disclosure have been characterized by multinuclear NMR spectroscopy, elemental analyses, X-ray crystallography and UV-Vis and Fluorescence spectroscopy. Table 1 contains the crystallographic data for 8 and 12. NMR resonances and couplings exhibited by germoles 2-12 are within expected values. Table 1 contains the crystallographic data for 8 and 12.

TABLE 1

Crystallographic Data and Structure Refinement for Compounds 8 and 12

| | 8 | 12 |
|---|---|---|
| Formula | $C_{44}H_{28}F_2Ge$ | $C_{56}H_{40}GeP_2$ |
| Fw | 667.29 | 847.41 |
| cryst size/mm | 0.32 × 0.33 × 0.38 | 0.40 × 0.60 × 0.80 |
| cryst syst | Triclinic | Triclinic |
| space group | pT | pT |
| a/Å | 10.555(2) | 11.4828(14) |
| b/Å | 11.095(2) | 12.9012(13) |
| c/Å | 15.680(3) | 18.022(2) |
| α/deg | 92.23(3) | 71.258(3) |
| β/deg | 104.77(3) | 77.857(4) |
| γ/deg | 113.52(3) | 64.911(4) |
| V/Å$^3$ | 1607.5(8) | 2281.2(4) |
| $D_{calcd}$/g cm$^{-3}$ | 1.379 | 1.234 |
| Z | 2 | 2 |
| abs coeff/mm$^{-1}$ | 0.996 | 0.778 |
| θ range/deg | 1.36 to 34.02 | 1.20 to 24.99 |
| reflns collected/indeprefns | 50264/12224 | 22480/7943 |
| | [R(int) = 0.027] | [R(int) = 0.041] |
| abs correct | numerical | numerical |
| max. and min. transm | 0.7467 and 0.6576 | 1.000 and 0.8625 |
| final R indices [I > 2σ(I)] | 0.0395 | 0.0390 |
| R indices (all data) | 0.1121 | 0.1310 |

Figure 3A:
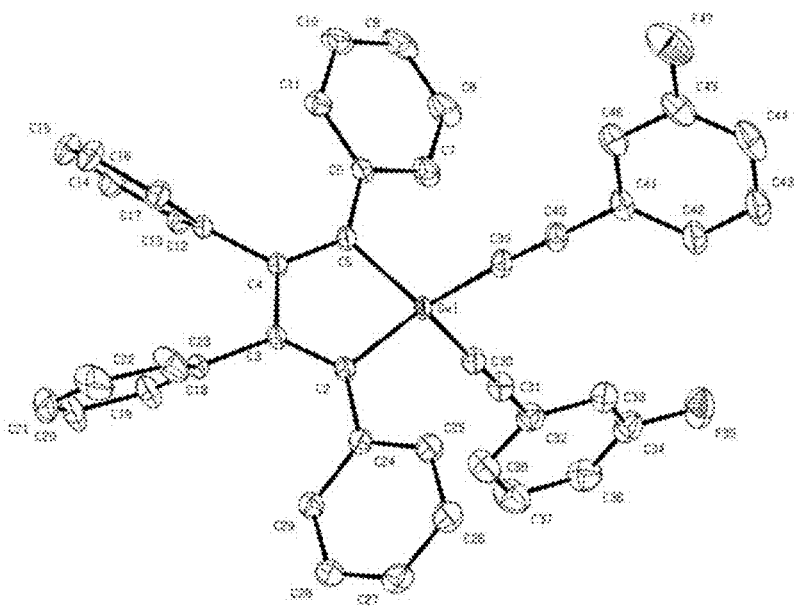
FIG. 3A shows the selected bond distances (Å), angles (deg), and torsions (deg) for item 8 in FIG. 2. Thermal ellipsoids are shown at the 50% probability level: Ge 1-C30=1.890(2), Ge 1-C39=1.897(2), Ge 1-C2=1.954(1), Ge 1-C5=1.940(2), C2-C3=1.362(2), C3-C4=1.512(2), C2-Ge 1-C5=91.83(6), Ge 1-C2-C3=106.2(1), Ge 1-C5-C4=105.8(1), C2-C3-C4=117.5(1), C3-C4-C5=1186(1), C30-Ge 1-C39=105.68(7), Ge 1-C2-C24-C25=36.5(2), Ge 1-C5-C6-C7=30.3(2), C2-C3-C18-C19=−113.9(2), C5-C4-C12-C13=61.8(2).
Figure 3B:
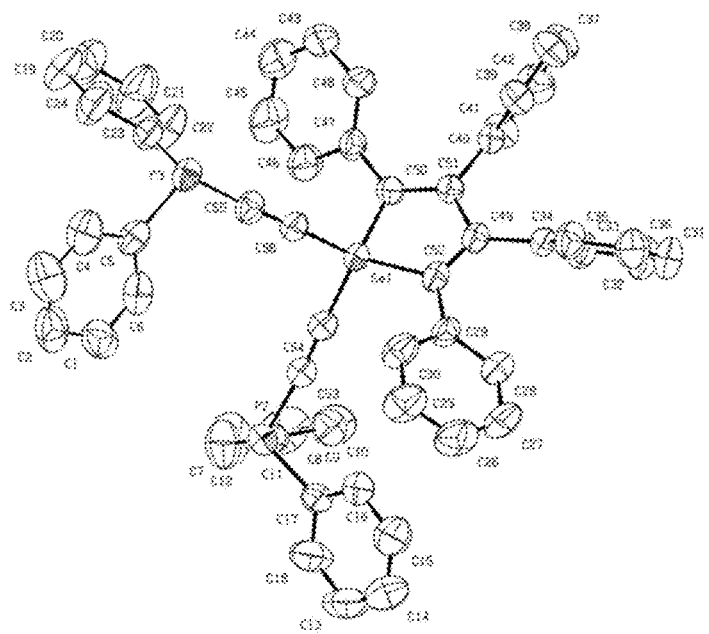
FIG. 3B shows the selected bond distances (Å), angles (deg), and torsions (deg) for item 12 from FIG. 2. Thermal ellipsoids are shown at the 50% probability level and the hydrogen atoms and the disorder on item 12 from FIG. 2 have been omitted for clarity: Ge 1-C50=1.929(2), Ge 1-C52=1.940(3), C49-C51=1.516(4), C50-C51=1.349(4), Ge 1-C54=1.897(4), Ge 1-C56=1.904(4), P2-C53=1.774(4), P3-C55=1.74(1); C50-Ge 1-C52=91.5(1), Ge 1-C50-C51=106.6(2), C50-C51-C49=117.9(3), C51-C49-C52=117.3(3), C54-Ge 1-C56=105.5(1), Ge 1-C50-C47-C46=−48.7(4), Ge 1-C52-C29-C30=−35.7(4), C52-C49-C34-C35=−56.7(5).

The molecular structures of compounds 2-12 were confirmed by X-ray crystallography. The molecular structures of compounds 8 and 12, respectively, which are exemplary germoles of the present disclosure, are illustrated in FIGS. 3A and 3B. FIGS. 3A and B illustrate the highly twisted conformation that the phenyl substituents assume relative to the germacyclopentadiene core. The peripheral phenyl substituents on the ring carbons are twisted out of plane with respect to the ring core and are twisted with the same sense within the compound. The averaged dihedral angle for the phenyl substituents on the 2,5-ring carbons for 2, 4-5, and 7-12 is ca. 38° and for the 3,4-ring carbons ca. 63°. The dihedral angles reported for 1,1-diphenyl-2,3,4,5-tetraphenylgermole for the 2,5-ring carbon substituents were 0.7° and 46.1°, while the 3,4-ring carbon substituents were 96.8° and 63.4°, respectively.

An analysis of the data obtained from the crystal structures suggests that the dihedral angles of 2, 4-5, and 7-12 are more similar to those in tetraphenyl-substituted siloles than the other germole derivatives characterized by Mullin et al. Inorg. & Organomet. Poly. Mater. 2007, 17, 201-203; Tracy et al., Chem. 2005, 44, 2003-2011. As a result of these similarities, modifications at the 2,5- and 3,4-positions of these germoles may be related to similar effects on the electronic and optical properties that have been observed in siloles.

TABLE 2

Selected Torsion Angles (Degrees) of compounds 8, 9, and 11

| Phenyl substituent attached to ring carbon | 8 | 9 | 11 |
|---|---|---|---|
| C1 | Gel-C14-C15-C16 31.3(3) | Gel-C2-C24-C25 33.4(2) | Gel-C31-C17-C35 −27.3(1) |
| C2 | C14-C13-C21-C22 63.4(3) | C2-C3-C18-C19 59.1(2) | C31-C11-C42-C15 −59.1(1) |
| C3 | C13-C12-C27-C28 68.8(3) | C3-C4-C12-C17 65.4(2) | C11-C30-C19-C37 −65.9(1) |
| C4 | Gel-C11-C33-C38 36.3(3) | Gel-C5-C6-C11 42.7(2) | Gel-C21-C3-C39 −46.6(1) |

Selected bond lengths and angles illustrate the general agreement of the geometric parameters for 2, 4-5, and 7-12. The average bond length is 1.938 Å for the germoles reported herein. The average C=C and C—C bond lengths of the central ring for 2, 4-5, and 7-12 are 1.357 Å and 1.511 Å, respectively. The average Si—C bond length was reported to be 1.869 Å while the average C=C and C—C bond lengths were 1.363 Å and 1.494 Å, respectively. The exocyclic Ge—C bond lengths are 1.895 Å and 1.893 Å. The C2-Ge—C5 bond angle of the central ring for 2, 4-5, and 7-12 is 91.5°.

The absorption spectra for 0.01 mM solutions of germoles 2-12 in methylene chloride were measured. All of the germoles 2-12 exhibit an absorption maximum between 364-369 nm. Germoles 2-12 weakly emit in the region of 478-488 nm in solution at room temperature with quantum yields that range from 0.0046-0.0071 ($\lambda_{ex}$=370). Under similar experimental conditions, germoles 2-12 exhibited quantum yields ca. 3× greater than either 1,1-dimethyl- or 1,1-diphenyl-2,3,4,5-tetraphenylgermole for which the reported quantum yields were 0.0015 and 0.0026, respectively.

TABLE 3

Absorption and Emission Data for 0.01 mM CH$_2$Cl$_2$ Solutions of 2-12 at Room Temperature ($\lambda_{ex}$ = 370)

| Germole | Absorption λ (nm) | Emission λ (nm) | $\Phi_F$* |
|---|---|---|---|
| 4 | 364 | 480 | 0.00457 |
| 3 | 365 | 478 | 0.00570 |
| 5 | 365 | 482 | 0.00464 |
| 9 | 366 | 485 | 0.00578 |

TABLE 3-continued

Absorption and Emission Data for 0.01 mM CH$_2$Cl$_2$ Solutions of 2-12 at Room Temperature ($\lambda_{ex}$ = 370)

| Germole | Absorption λ (nm) | Emission λ (nm) | $\Phi_F$* |
|---|---|---|---|
| 7 | 366 | 486 | 0.00508 |
| 6 | 367 | 485 | 0.00569 |
| 10 | 368 | 487 | 0.00627 |
| 2 | 369 | 483 | 0.00582 |
| 8 | 369 | 488 | 0.00538 |
| 12 | 369 | 487 | 0.00706 |
| 11 | 369 | 486 | 0.00689 |

Consistent with the trend observed for siloles, manipulations of the 1,1-substituents imposed a similar shift to longer absorption maxima as the substituents directly attached to the germanium center increased in electronegativity. Among a series of germoles possessing the same 1,1-substituents, the UV absorption maxima red shifts in the order of Me (350 nm)<Ph (358 nm)<C≡CH (362 nm)<C≡C—R (364-369 nm for 2-12).

Figure 4:
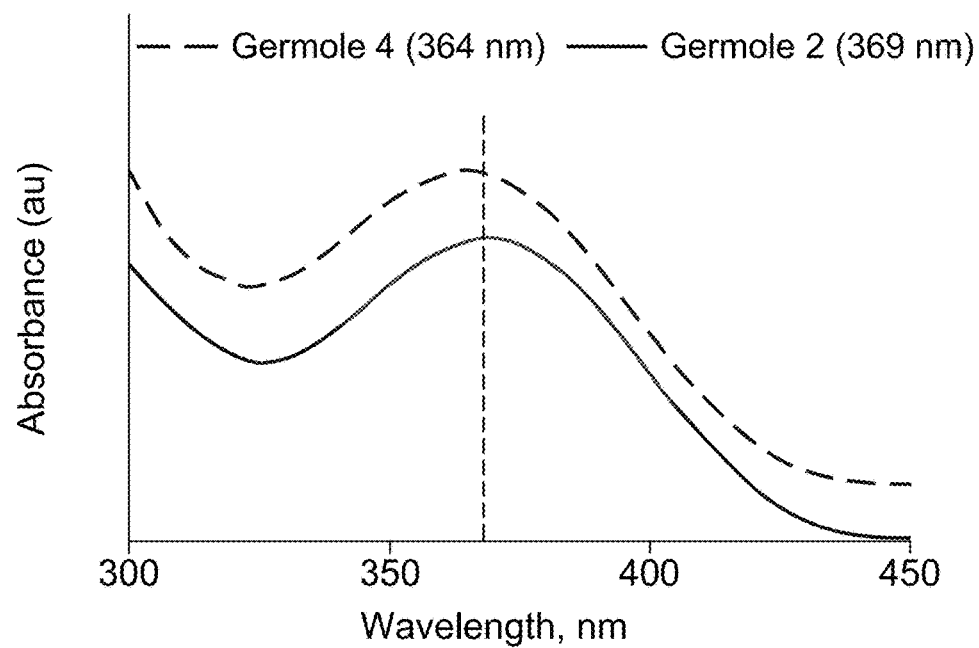
FIG. 4 includes the absorption spectra for the methylene chloride solutions of germoles 2 and 4 from FIG. 2, which represent the range of the UV absorption maxima.

Referring to FIG. 4, which is the graph of the absorption spectra for the methylene chloride solutions of germoles 2 and 4, substitutions on the β-position of the triple bond (the terminal position of the alkyne) reflect a modest red shift as more electronegative groups are introduced. This is in contrast to silole derivatives possessing alkynyl substituents at the 1,1-positions where the absorption and emission wavelengths remained unchanged despite varying the β-substituents of the alkyne from hydrogens to phenyls. Such data suggests a greater sensitivity in germoles to the identity of the substituents, even those that are at more remote bonds from the germanium center and may allow more control in fine-tuning the electronic properties.

The solid-state photoluminescence is measured using a thin layer chromatography (TLC) method developed by Chen et al, Chem. Mater. 2003, 15, 1535-1546, incorporated by reference to the extent it is consistent herewith, and the emission wavelengths are summarized in Table 4. The thin layer of all the germoles absorbed on the TLC plate fluoresce intensely in the blue-green region. The intensity of the PL emission significantly increased compared to the corresponding weakly emissive solutions. The trend in the red shift in the emission wavelengths was not readily apparent. The germoles of the present disclosure exhibited. Stokes shifts between 117-132 nm. These values are consistent with the reported Stokes shift for siloles which vary between 120-129 nm, as well as those reported for 1,1-dimethyl- or 1,1-diphenyl-2,3,4,5-tetraphenylgermole, 117 nm and 130 nm, respectively. Stokes shifts greater than 100 nm are necessary for applications that require ultra-high sensitivity such as fluorescence imaging measurements and bioprobes for protein detection and quantification.

TABLE 4

Solid-State Emission Data for 2-12 at Room Temperature (λex = 370)

| Germole | Emission λ (nm) | Stoke's Shift (nm) |
|---|---|---|
| 6 | 484 | 117 |
| 3, 4, 7, 9 | 485 | 120, 121, 119, 119 |
| 2 | 486 | 117 |
| 11 | 490 | 121 |
| 5 | 492 | 127 |
| 8, 12 | 493 | 124 |
| 10 | 500 | 132 |

Figure 5A:
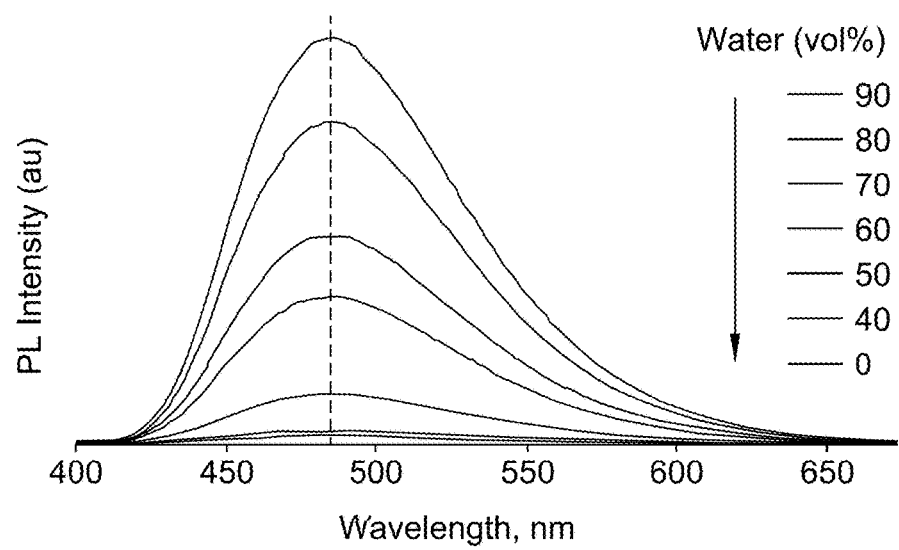
FIG. 5A shows the PL spectra for 0.01 mM of item 2 from FIG. 2 in pure acetone and acetone-water mixtures at room temperature ($\lambda_{ex}$=370 nm)
Figure 5B:
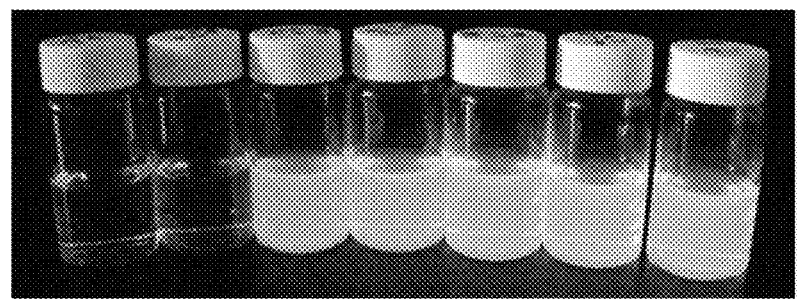
FIG. 5B is a photo of the solutions of item 2 from FIG. 2 in pure acetone (far left) and acetone-water mixtures (40%, 50%, 60%, 70%, 80%, and 90% respectively) which correlates with the graph of the PL spectra.

The present disclosure is also directed to the AIE effect of the germoles. Referring to FIGS. 5A and 5B, which illustrate the AIE effect in germole 2 at various quantities acetone/water mixtures. Germole 2, which is soluble in acetone as verified by dynamic light scattering measurements but is insoluble in water, is first dissolved in pure acetone and then a specified amount of water is added. Once the water is added to the mixture, the solubility of 2 is reduced causing aggregation which results in an increase in the photoluminescence. As illustrated by FIGS. 5A and 5B, the dilute acetone solution of 2 is weakly emissive; however, as the proportion of water to acetone increased in the mixed solvent system, the photoluminescence significantly increased. A similar increase in photoluminescence upon addition of water to either an acetone or acetonitrile solution of the germole has also been observed for 6, 8, 11, and 1,1-diethynyl-2,3,4,5-tetraphenylgermole. All variations within the mixed solvent system exhibited similar spectral profiles with minimal shifting of the emission wavelength maximum, which is consistent with similar siloles and germoles. Typically, aggregation results in a red shift of the emission wavelength. Noteworthy is the indication that the onset of AIE begins at ca. 30% water content within the mixed solvent system although the phenomenon is modest. Known studies examined similar concentrations of 1,1-dimethyl- and 1,1-diphenyl-2,3,4,5-tetraphenylgermole in a variety of mixed solvent-water systems and reported the earliest occurrence of AIE was between 60-70% water content in a mixed water-dioxane system (Mullin et al., Inorg. & Organomet, Poly. Mater. 2007, 17, 201-213).

Figure 6:
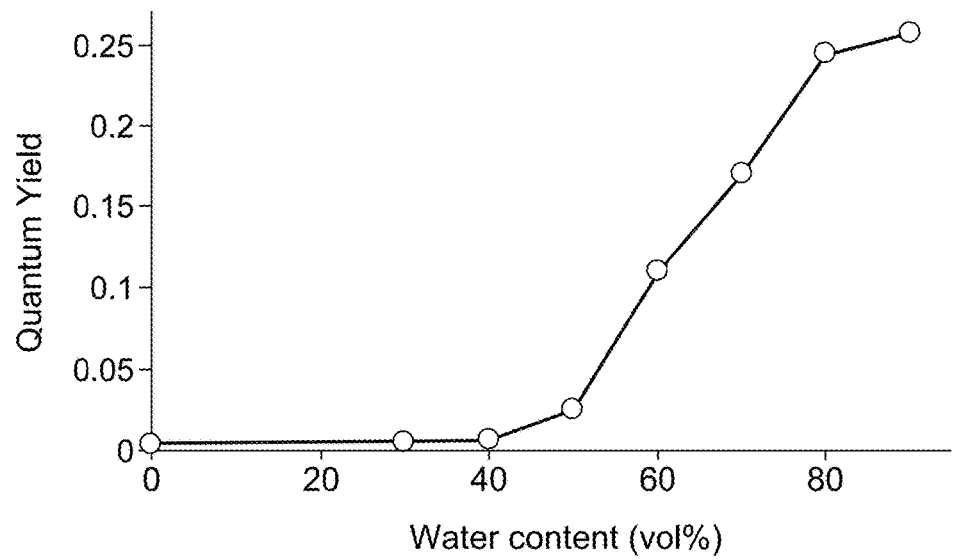
FIG. 6 illustrates the quantum yield of item 2 from FIG. 2 vs. the water content of the mixed acetone-water systems.

FIG. 6 correlates the increase in the PL intensity of 2 with an increase in the emission quantum yield. In FIG. 6, the quantum yields in the acetone and acetone-water mixtures are calculated using 9,10-diphenylanthracene as a standard. The quantum yield of the acetone solution of 2 is 0.0040. A modest increase in the quantum yield to 0.0050 is observed at a water content of ca, 30% implying that intramolecular motions of 2 are already being minimized. Restriction of the intramolecular motions of 2 results in increased PL intensity (the AIE effect), which although not discernible by the naked eye, is detectable with instrumentation. The increased PL intensity is supported by the increase in quantum yield. When the water content of the acetone-water system is 90%, the quantum yield increases to 0.26, which is 65 times higher than the acetone solution.

Figure 7:
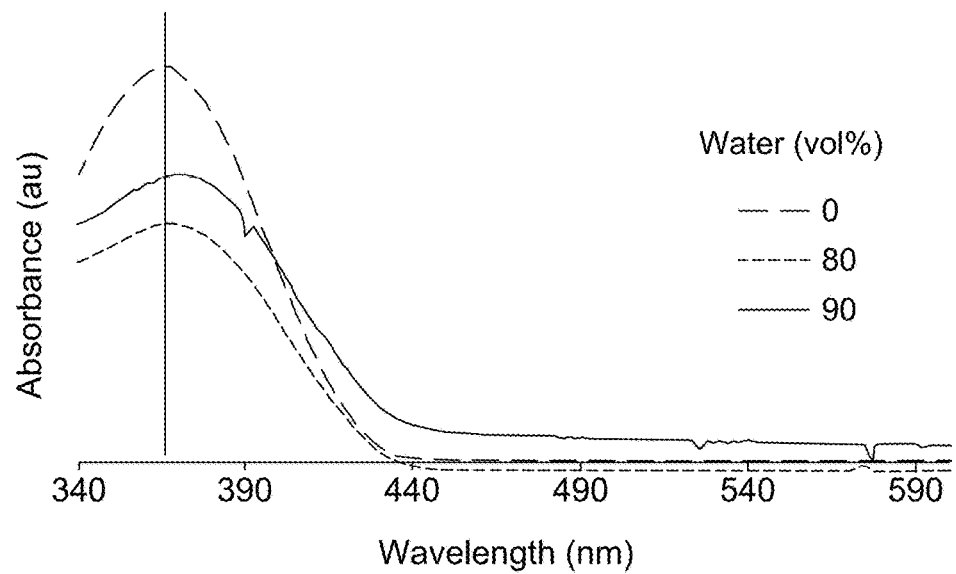
FIG. 7 illustrates the absorption spectra of 0.01 mM of item 2 from FIG. 2 in the mixed acetone-water solvent systems.

Referring to FIG. 7, which includes the absorption spectra of 0.01 mM 2 in the mixed acetone-water solvent systems, all variations within the mixed acetone-water solvent system exhibited a similar absorption spectral profile with broad absorption bands that trail into the long wavelength region and a slight red shift of the wavelength maximum. The spectral profiles imply that 2 has aggregated in the acetone-water mixtures as both broad absorption bands and red shifts are characteristic optical responses related to the Mie scattering effect associated with the presence of small, metallic particles. Dynamic light scattering measurements taken within ca. 40 minutes of preparing the samples also suggest that 2 had aggregated into nanoparticles with average sizes of 47 and 74 nm in the acetone-water mixtures with water contents of 80% and 90%, respectively.

Figure 8A:
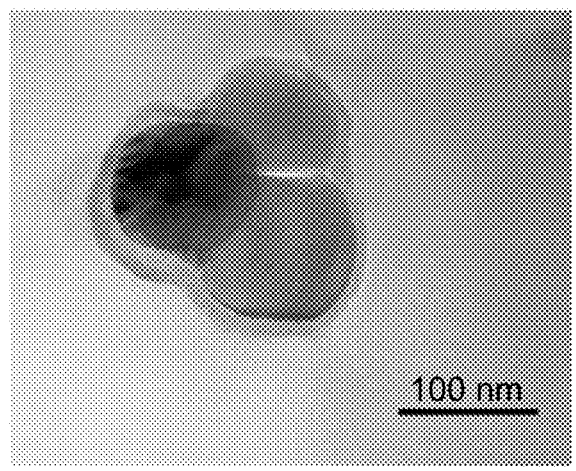
FIGS. 8A to 8C are TEM images of item 2 from FIG. 2, TEM images of item 2 from FIG. 2 illustrate the small aggregate clusters (A) and larger aggregate clusters (B) that were observed in the water-acetone mixture containing 90% water; the electron diffraction pattern (C) exhibited by aggregates in the 10% water-90% acetone mixture.
Figure 8B:
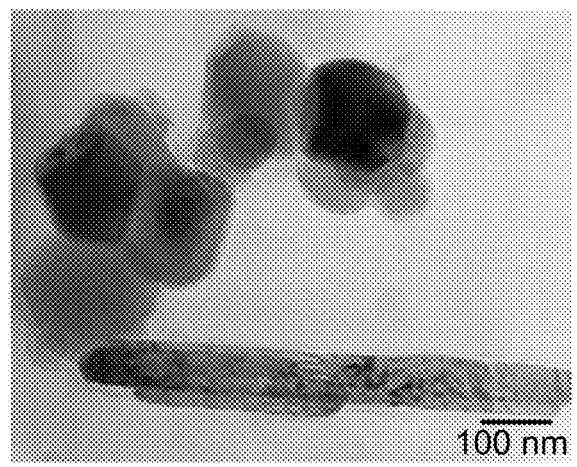
Figure 8C:
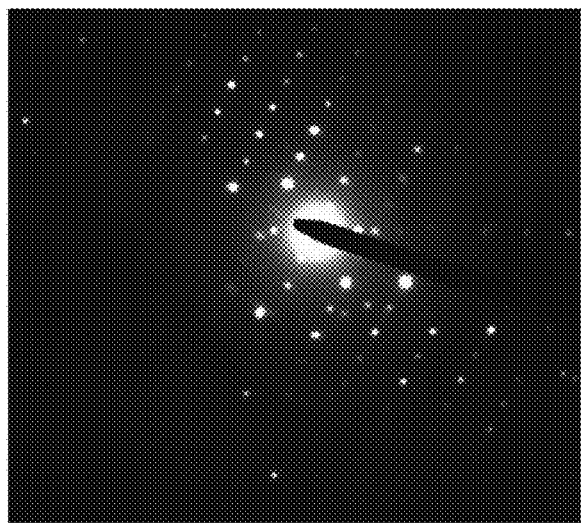

Refer to FIGS. 8A to 8C, which include TEM images of 2 as small and large aggregate clusters in water-acetone mixture, to investigate the nature of the aggregate formation in the acetone-water mixtures. In the 10% acetone-90% water mixture, the TEM images of 2 depicted the formation of nanoparticles with individual dimensions that are closer to 100 nm that aggregate in small clusters (FIG. 8A). The smaller aggregate clusters are more prevalent than the larger aggregate clusters; an example of one of the larger aggregate clusters is given in FIG. 8B.

The crystalline nature of the particles is confirmed by electron diffraction patterns (FIG. 8C). As in solid phase crystals, it is reasonable to conclude that the aggregates pack in an arrangement which minimizes $\pi$-$\pi$ stacking of any planar segments of the germole. Lack of intermolecular $\pi$-$\pi$ interactions as well as an increased restriction of any molecular motions imposed by the crystalline lattice would promote the photoluminescence observed in the acetone-water mixtures.

The present disclosure is further directed to the use of the germoles as chemosensors for the detection of volatile organic compounds. Specifically, the germoles, 2, 8, and 1,1-diethylnyl-2,3,4,5-tetraphenylgermole were tested as potential chemosensors for the detection of volatile organic compounds (VOCs) such as acetone. The photoluminescence was monitored as thin films of the germoles that were exposed to acetone vapor.

Figures 9A, 9B, 9C:
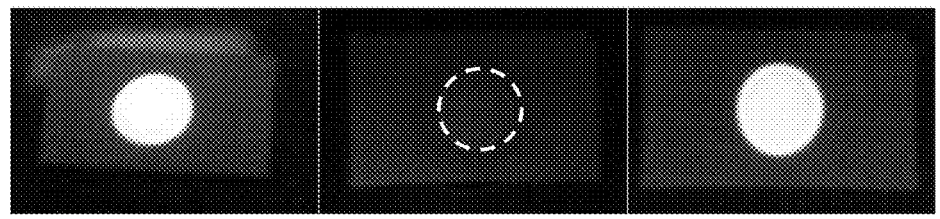
FIGS. 9A to 9C are photos of the TLC plates of item 8 from FIG. 2: (A) prior to solvent exposure, (B) after exposure, and (C) after the solvent evaporated.

Referring to FIGS. 9A to 9C, which are photos of TLC plates with germole 8 before and after exposure to acetone, TLC plates were spotted with ~$10^{-3}$ M methylene chloride solutions of the germoles and allowed to thoroughly dry in air. As can be seen in FIG. 9A, the thin film of 8 intensely fluoresces. Upon exposure to acetone vapor, the emission is rapidly quenched (FIG. 9B). This is consistent with the acetone vapor condensing on the TLC plate and dissolving the germole which quenches light emission, representing the "OFF" switch. Once the acetone vapor evaporates, the emission resumes (FIG. 9C) suggesting that the germole aggregates and once again emits light, representing the "ON" switch. This luminescence switch behavior has been observed for all three of the germoles tested and can be repeated multiple times without diminishing the light emission.

The solid state photoluminescence of AIE(E) molecules can be further enhanced by crystallization which commonly occurs during the annealing process of thin films in OLEDs and is detrimental to the luminescence of conventional luminophors (ACQ effect). According to the crystallization-enhanced emission (CEE) theory, the intramolecular rotations of the peripheral aryl substituents are even more restricted within a crystal lattice as compared to an amorphous solid which can enhance light emission by several orders of magnitude. The RIR mechanism gives rise to the AIE(E) phenomenon which has been observed in Group 14 metalloles containing aryl substituents. The strong emission in both the crystalline and amorphous solid states exhibited by Group 14 metalloles makes them ideal candidates for a variety of applications such as active layers for EL devices and as chemical and biological sensors.

In the packing arrangement of hexaphenylsilole (HPS) and 1,1-diethynyl-2,3,4,5-tetraphenylsilole, multiple CH-$\pi$ bonds were identified that were propose to further aid in restricting intramolecular motions of the aryl substituents by locking the conformation within the crystalline lattice which enhanced the PL emission (Dong et al., Inorg. Organomet. Polym. 2007, 17, 673-678).

Figure 10A:
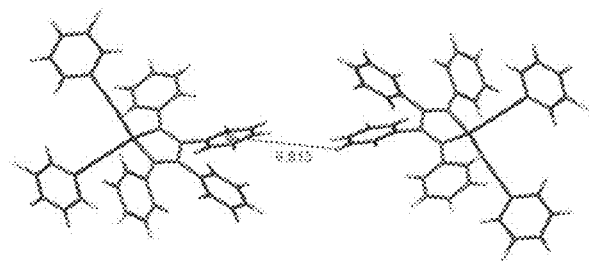
FIGS. 10A and 10B illustrate the packing arrangement of crystalline item 8 from FIG. 2: (A) showing the intermolecular distance between two molecules of 8 (6.9 Å) at the 3,4-diphenyl substituents; (B) showing the interplane separation between two molecules of item 8 from FIG. 2 and the two shortest C—H-π hydrogen-bonding interactions of 3.0 and 2.7 Å.
Figure 10B:
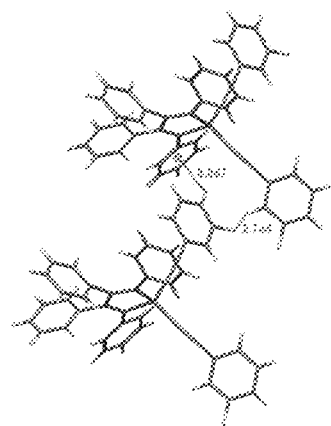

Referring to FIGS. 10A and 10B, which closely examine the packing arrangement of the crystals of 8 for evidence of any cooperative bonding interactions, the crystal structure of 8 illustrates that adjacent molecules pack in such a way that the phenyl substituents are practically orthogonal and cannot overlap. The closest distance between the 3,4-phenyl substituents of two adjacent molecules of 8 is 6.9 Å (FIG. 10A), which is too great a distance for any $\pi$-$\pi$ stacking or CH-$\pi$ interactions. The ring cores are staggered with respect to one another with an interplane distance between the germole cores of 10.5 Å (FIG. 10B), too great a distance for any intermolecular interactions. There are, however, multiple CH groups as well as fluorine atoms present in 8 that may participate in non-conventional, weak CH-π hydrogen bonding in two regions within the packing arrangement. Both potential cooperative interactions involve the substituted phenyl ring of one of the 1,1-substituents with the phenyl substituents on an α-carbon in the ring core and another 1,1-substituent of a second molecule located directly above (FIG. 10B). The distances between these segments are 3.0 Å and 2.7 Å, respectively. These measurements are within hydrogen-bonded and intermediate (type CH—X) intermolecular approaches of ca. 3.0 Å which were demonstrated for edge-to-face orientations in several siloles. Hence crystallization of 8 does not diminish photoluminescence. All the symmetric 1,1-disubstituted germoles exhibit strong solid luminescence in both the amorphous and crystalline phases. Research Summary for Unsymmetrical 1,1'-disubstituted germoles, Germafluorenes, Germa-rhodamines/Germa-Fluoresceins and Germapins Research strategies for designing luminescent Group 14 molecules describe the preparation of a) unsymmetrical 1,1'-disubstituted germoles and b) functionalized germafluorenes, germa-fluoresceins/germa-rhodamines, and germapins. These synthetic pathways build on a variety of established reactions and allow incorporation of structural features that promote aggregation-induced emission (AIE (E)). Mechanistic studies of molecules that exhibit the AIE(E) effect indicate that their unique propeller-like structures are vital to photoluminescence in the solid state. These molecules possess multiple peripheral aryl substituents that function as "blades" that rotate around single or double bond axles that link them to a central conjugated core. Steric congestion restricts the intramolecular rotations (RIR) of the peripheral aryl substituents causing the groups to twist relative to the core. Hence, the propeller-like shape prevents π-π stacking interactions with neighboring fluorophores in condensed phases such as aggregates or the solid state minimizing excimer formation and resulting in strong light emission.

These luminophors possess exceptional optoelectronic properties and are excellent candidates for solid state applications as components in OLEDs (OFETs), host materials, and solar cells. Major emphasis is being placed on the development of air stable blue and the more rare red light-emitting molecules with high electron affinities and mobilities that meet specifications for organic semiconducting materials.

The present disclosure is directed to a series of 1-phenyl-1'-substituted germoles, where the 1'-substituent can be a variety of (aryl)ethynyl groups bound to the Ge center. Groups were selected for their ability to enhance emission in the solid state through AIE(E). The present disclosure is also directed to the synthesis of germafluorenes, germanium-based fluoresceins/rhodamines, and germapins. Synthetic methods were used to allow for structural modification of the organic framework, the central ring and the germanium center of these larger heterocycles to target both blue and red-emitting molecules for solid state applications. Many of the optoelectronic properties of these molecules are intricately tied to their electronic structures which can be tuned by incorporating a variety of functional groups, fusing aromatic rings, or introduction of heteroatoms.

Unsymmetrical 1,1'-disubstituted Germoles

One aspect of the present disclosure involves the synthesis of new unsymmetrical, 1,1'-disubstituted-2,3,4,5-tetraphenyl- and 2,3,4,5-tetra(aryl)germoles to examine both the steric and electronic effects of the substituents on the ring and at the Ge center on the solid state luminescent properties and efficiencies. Unsymmetrical 1,1'-germoles exhibit significantly higher quantum efficiencies in the solid state than their symmetrical congeners. Related siloles differing in 1,1'-substitution exhibited higher solid state quantum efficiencies compared to the symmetrical 1,1-substituted siloles due to the higher difficulty in packing compactly in the solid state. In addition, the use of phenyl substituents on the germanium center lowers the LUMO energy level, an effect that has been observed with siloles which has been attributed to extended $\sigma^*$-$\pi^*$ conjugation between the silicon center and the phenyl ring.

1-chloro-1-phenyl-2,3,4,5-tetraphenylgermole 42 (FIG. 11, Scheme 4) can be produced by addition of commercially available PhGeCl$_3$ in a reaction analogous to that used to produce germole 29.

Other diarylacetylenes (PhC≡CPh, PhC≡CSiPr$_3$ and ArC≡CPh (Ar=2,6-diisopropylphenyl)) can be reacted with lithium metal in a similar fashion as described for 1 for the construction of new 1,1'-disubstituted-2,3,4,5-tetra(aryl) germoles. A palladium-catalyzed one-pot synthesis of symmetric diarylacetylenes is utilized to prepare precursors analogous to germole 1. 1-chloro-1-phenyl-2,3,4,5-tetra(aryl)germoles utilizing the symmetrical diarylacetylenes, ArC≡CAr (Ar=p-tolyl, biphenyl, and p-methoxyphenyl) is prepared. Scheme 4 shows the synthetic routes that produce a series of new 1,1'-unsymmetrically substituted germoles beginning with germole 13, Related 1-aryl-1-chloro-2,3,4,5-tetraphenylgermoles were prepared by direct reaction of with an aryl-Grignard reagent, ArMgX (Ar=p-(NMe$_2$)C$_6$H$_4$, p-MeC$_6$H$_4$, C$_6$F$_5$). This aspect of the present disclosure builds functionality at the 1-germole position via, the Ge—Cl unit. Reaction of germole 13 with arylalkynyllithium reagents would produce new germoles 15a-o. Alternatively, palladium-catalyzed coupling reactions can be performed to introduce an array of different aryl groups by reaction of the 1-ethynyl group in 14 with an aryl iodide or bromide if the desired substituted terminal alkynes are not commercially available. Germole 14 has not been reported in the literature, but the corresponding silole has been prepared by the analogous reaction shown in Scheme 4.

The use of the ethynyl group bound directly to the germole core is desirable as it extends the conjugation of the metallole ring and enables incorporation of a variety of aryl substituents that would be too sterically demanding if bound directly to the germanium center. The Sonogashira-type coupling described in Scheme 4 is tolerant of a variety of functional groups. The synthesis of related unsymmetrical 1,1'-disubstituted siloles have been reported utilizing Sonogashira coupling reactions but the preparation of unsymmetrical 1,1'-disubstituted germoles is limited. Related oligomers from 1,1-diethynyl-2,3,4,5-tetraphenylsilole and aryl and heteroaryl bromides and iodides have been prepared in the presence of a Pd catalyst. In one aspect of the present disclosure, ethynyl-substituted aromatics and thiophenes which are suitable for the synthetic route shown in Scheme 4 were prepared (See FIG. 11).

With the aim of developing high efficiency solid state luminescence in Group 14 heterocycles, structural modifications were explored that promote the AIE(E) processes. Many of the structural prerequisites that promote these two processes can be readily incorporated into Group 14 containing heterocycles to minimize the problems that are often associated with luminogens that quench upon aggregation thus rendering them ineffective for solid state applications. By studying the structure-property relationship of Group 14 heterocycles, an array of highly luminescent molecules that span a wide range of the visible spectrum including the blue and more rare red-emitting regions were prepared. Based on the AIE(E) processes, new germanium heterocycles such as germafluorenes, germanium-based fluorescein/rhodamine analogs, and germapins which all possess structural similarities to known AIE(E) germapins were prepared. Synthetic procedures are described below that allow for covalent decoration of germanium heterocycles that also include examples with heteroatom substituents. Although processes such as donor-acceptor push-pull interactions, J-aggregate formation, or twisted intramolecular charge transfer (TICT) between polar functional groups do not activate the AIE(E) effect, incorporation of these groups into the heterocycles allows for control of the emission color providing luminophors that cover the entire visible spectrum.

Germafluorenes

In order for materials to find practical applications as electron-transporting or emissive layers as thin films in semiconducting and electronic devices, a luminophor should exhibit two major characteristics: fast electron injection/transport abilities and high fluorescence quantum yield ($\Phi_F$) in the solid state. Few organic molecules can exhibit both air stability and high electron mobility. Additionally, many organic fluorophores experience quenching upon aggregation (ACQ effect) thus rendering them ineffective for solid state applications. The Group 14 heterocycles provide a unique solution to these problems. Studies have established the superior solid state properties of Group 14-based luminogenic molecules and materials particularly those of germafluorene, for electroluminescent applications compared to their carbon analogs. These air stable Group 14 heterocycles possess extremely low LUMO energies necessary for fast electron injection/transport abilities and high thermal stabilities while their aggregation-induced emission (AIE) properties allows for the development of luminophors whose aggregates fluoresce more strongly than their solutions. The Group 14 molecules described herein exhibit interesting and highly promising optoelectronic and chemical properties that enable them to participate in a number of electroluminescent device and chemosensor applications that will benefit technological advancements and safety benefits for society.

These superior optoelectronic properties have also been observed in related, but larger ring systems such as 9-sila- or 9-germafluorenes, respectively, which have become prominent building blocks in polymer-based materials. Efforts to improve upon these materials have provided insight into the potential of germanium-containing analogs which have been studied to a lesser extent despite exhibiting properties similar to silicon. This germanium heterocycle is an excellent blue light-emitting and host material. Germafluorenes have demonstrated significantly higher maximum luminescence efficiencies in the same polymer light-emitting diode (PLED) device configurations as that of silafluorene and the electrochemical redox behavior supports the presence of an even lower lying LUMO than that of silicon. This data supports the better electron injection and transfer abilities of germafluorene than that of its silicon analog.

The greater impact of germanium over silicon has also been demonstrated by higher power conversion efficiencies (PCE) when germafluorene copolymers were used as the active light absorbing layer or p-type material in inverted bulk heterojunction (BHJ) solar cells. In these systems, the redox behavior of germafluorene copolymer indicated a higher HOMO energy level than that of silafluorene under identical conditions translating into a larger energy gap between the HOMO (p-type material) and LUMO (n-type material) which is vital for the determination of the open circuit voltage of the solar cell. Similar results were obtained with Group 14 metalloles where calculated values for germole-containing oligomers indicated higher HOMO energy levels than those of siloles. As such, the synthesis and photo/electroluminescence properties of germanium heterocycles as active components in optical and electronic devices are beneficial.

In one embodiment of the present disclosure, the compounds are a series of substituted germafluorenes having the general formula (II)

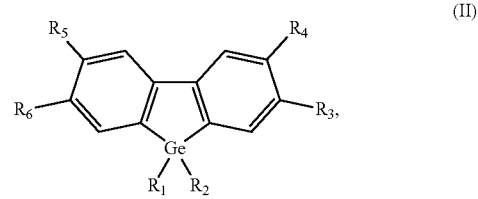

wherein $R_1$ and $R_2$ may be independently selected from the group consisting of aryl, alkyl, halide, alkynyl, and asymmetric derivatives thereof with two different groups at the Ge-center;

wherein $R_3$ and $R_6$ may be independently selected from the group consisting of Y and

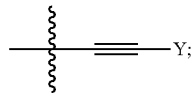

wherein $R_4$ and $R_5$ may be independently selected from the group consisting of $OCH_3$ and Y; and wherein Y is H,

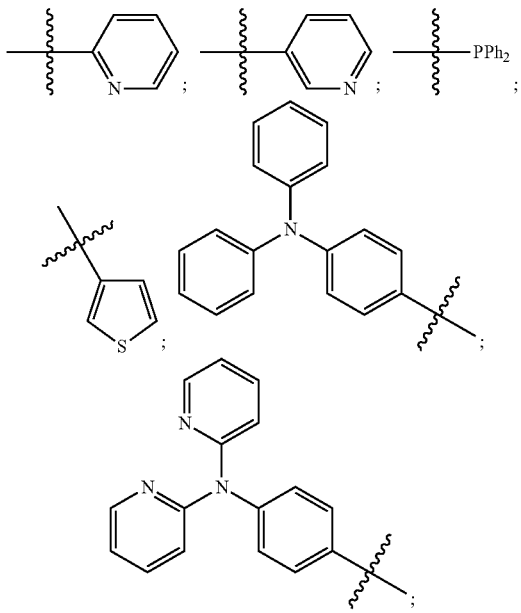

-continued

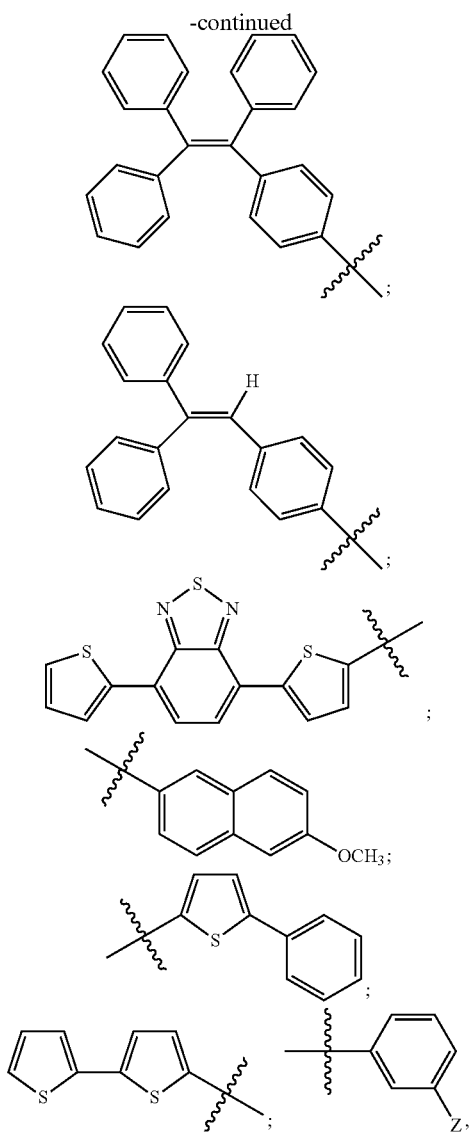

wherein Z is F, CH₃, or OCH₃:

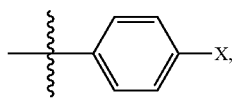

wherein X is H, CF₃, OPh, CH₃, Ph, OCH₃ or

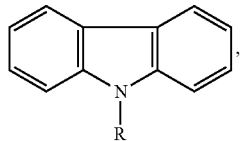

wherein R is aryl, alkenyl or alkynyl.

Figure 12:
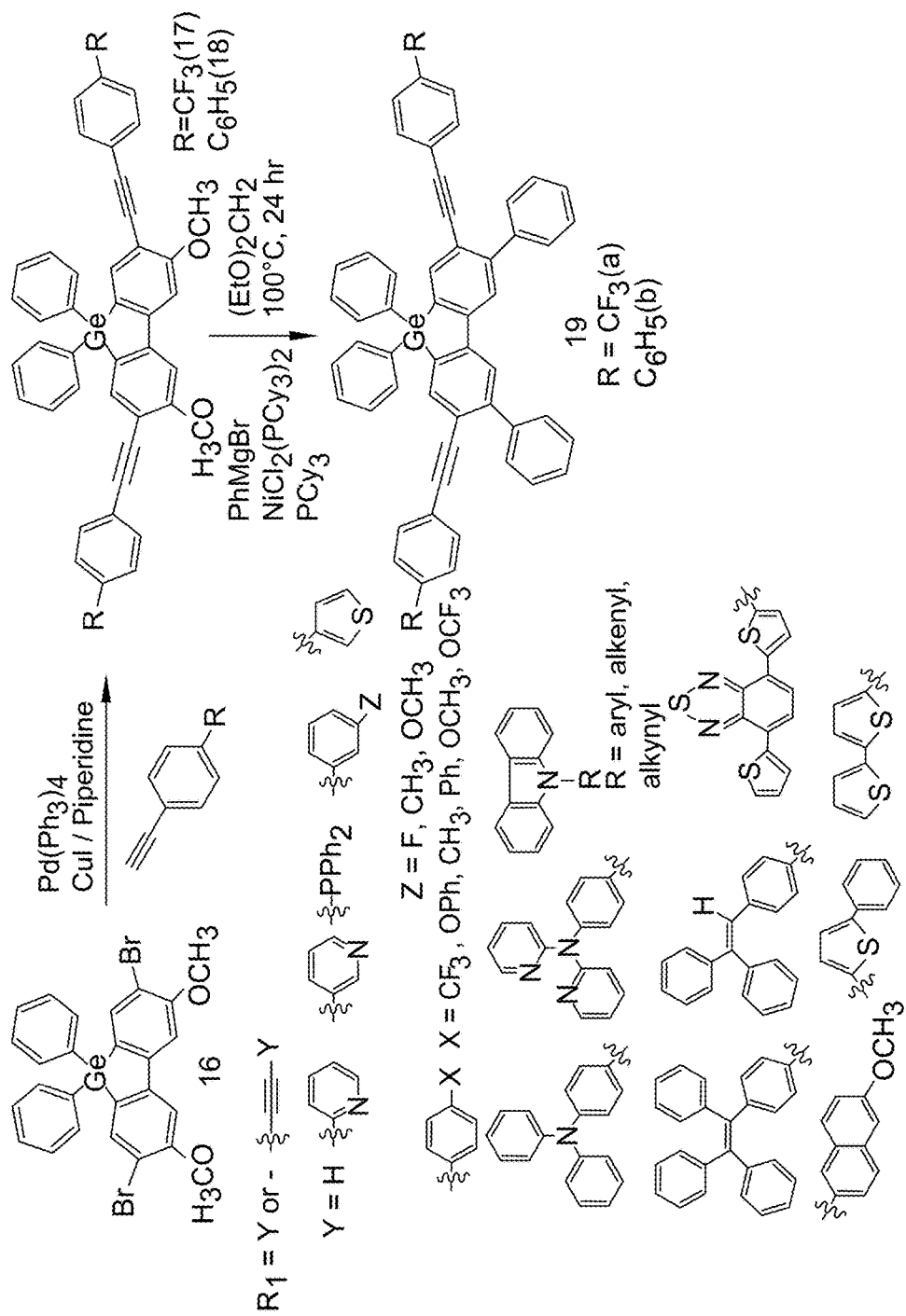
FIG. 12 illustrates an exemplary synthesis scheme for germafluorene compounds of the present disclosure.
Figure 13D:
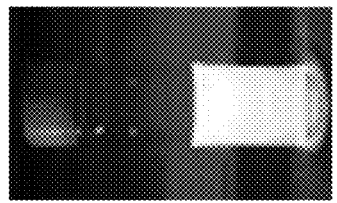
FIGS. 13A-D illustrate a comparison of the fluorescence between 9,10-diphenylanthrancene (ca. 1×10$^{-3}$M) (A) and decreasing concentrations of 2,7-bis((trifluoromethyl)-ethynyl)phenyl) germafluorene 1×10$^{-3}$ M (B), 1×10$^{-4}$ M (C), and 1×10$^{-5}$ M (d) in CH$_3$CN.
Figure 13C:
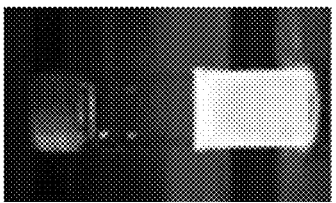
Figure 13B:
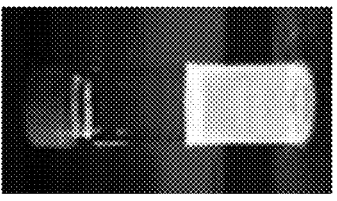
Figure 13A:
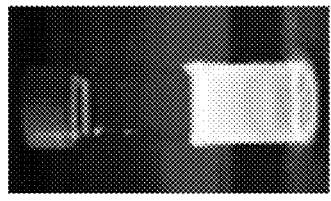
Figure 15:
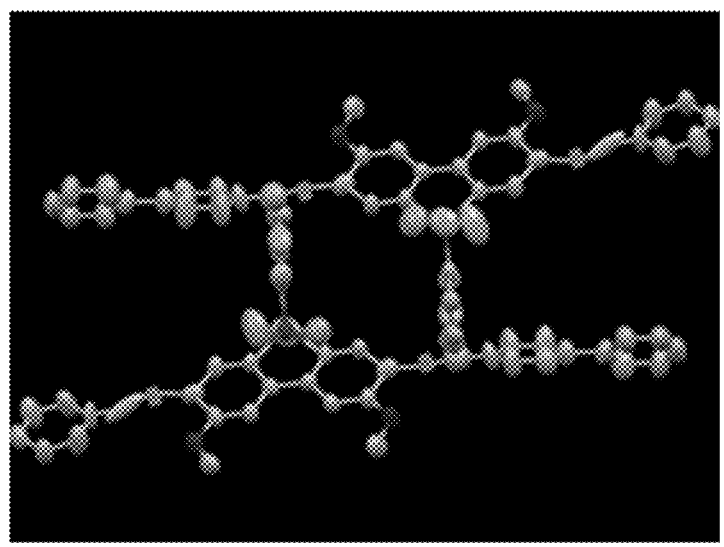
FIG. 15 depicts the crystal structure of one exemplary germafluorene of the present disclosure.

FIG. 12 illustrates an exemplary synthesis for germafluorenes, with additional substituting Ar groups. FIG. 15 depicts the crystal structure of one exemplary germafluorene.

Sila- and germafluorenes are of particular interest to this disclosure since they are increasingly being used as key building blocks in conjugated copolymer systems. The related polyfluorenes which have been used to construct high performance polymers suffer from a major disadvantage in that they are prone to oxidation at the C-9 carbon position upon heating resulting in a red shift in the emission, reduced emission efficiency and color degradation. Significant improvements in emission efficiency, enhanced electron injection and transport abilities as well as stable blue emission have been achieved by incorporating sila-, and germafluorene in place of fluorene in (co)polymers. In addition to these exceptional properties, thermogravimetric analysis (TGA) evaluation of germafluorene copolymers indicate good thermal stabilities that exceed 400° C.

Efforts by researchers have shifted to the development of single molecule germafluorenes for applications in organic electronic devices and thus a series of 2,7-disubstituted-3,6-dimethoxygermafluorenes was synthesized using a modified procedure reported by Huang for the preparation of 6,6'-dilithio-4,4'-dibromo-3,3'dimethoxybiphenyl from the corresponding 6,6-diodo-biphenyl precursor. Subsequent reaction with $Ph_2GeCl_2$ provided the target 2,7-dibromo-3,6-dimethoxygermafluorene. Germafluorene 16 was reacted with two different aryl-substituted alkynes (HC≡CAr) under standard Sonagashira cross-coupling conditions to afford two new 2,7-disubstituted(alkynyl)-3,6-dimethoxygermafluorenes 17 and 18 (FIG. 12). Other related silafluorene analogs have been prepared by a similar synthetic route.

Figure 14A:
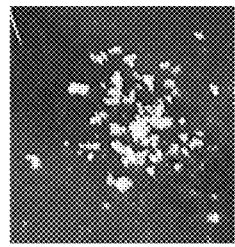
FIGS. 14A-C illustrate crystals of 2,7-bis((trifluoromethyl)-ethynyl)phenyl)germafluorene under ambient light (A) and UV light (B) and fluorescence of the thin film (C).
Figure 14B:
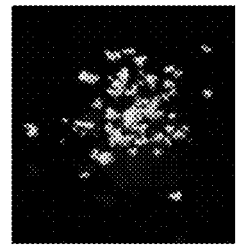
Figure 14C:
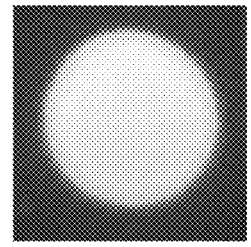

Investigations of germafluorenes 17 and 18 suggest that these compounds are AIEE molecules as they exhibit intense blue emission in solution ($\lambda_{abs}$~375 nm, $\lambda$em=426 nm) (FIGS. 13A-13D) as well as in the solid state (FIGS. 14A-14C). The germafluorenes are soluble in a wide range of common organic solvents which allow uniform thin films to be drop cast from standard solutions for future cyclic voltammetry and device fabrication studies. In the solid phase, the emission was measured at ca. 430 nm using a thin layer chromatography (TLC) technique. Determination of the fluorescence quantum yields in solution using anthracene in ethanol as a standard was undertaken. Germafluorene 17 exhibited a quantum yield of 0.77. Related silicon derivatives exhibit a slightly lower $\Phi_F$ value under similar conditions. Remarkably, these new 2,7-disubstituted germafluorenes demonstrated exceptional stability in air and solution. The absorption and emission maxima and intensity were unchanged for solutions stored in standard vials under ambient conditions after 2 years in $CH_3CN$ or acetone (FIGS. 13A-13D). Upon visual inspection, the luminescence intensity of the germafluorenes, even at more dilute concentrations, resembles a solution 9,10-diphenylanthracene, a common standard used for determination of fluorescence quantum yields. Germafluorene 17 demonstrated a high tolerance to photobleaching under high energy (254 nm) for prolonged periods of time.

The molecular structures for the two new germafluorenes 17-18 were confirmed by X-ray crystallography. FIG. 15 displays the molecular structure of 17 that exhibits an almost planar germanium containing central core which promotes efficient σ*-π* conjugation and as a result the alkynyl linker at the 2,7-positions can assume a flexible orientation. A significant separation is observed in the packing structure between molecules thus preventing intermolecular electronic interactions such as π-π stacking that would lead to luminescence quenching. The central core of the germafluorene ring system provides three sites for the study of structure-property relationships. In one aspect of the present disclosure, the use of phenyl substituents bound to the Ge center is disclosed since they provide steric congestion required to disturb packing arrangements that promote AIE (E) properties and enhance the thermal stability of the molecules. However, a variety of groups can be utilized to promote these properties including substituted aryl groups (i.e. p-tolyl), and linear hydrocarbon groups such as n-butyl. Functionalization at the para-positions can be achieved by replacement of the methoxy groups with phenyl, p-tolyl, or mesityl substituents utilizing a Ni-catalyzed cross-coupling reaction involving the corresponding aryl Grignard reagent (FIG. 12, 19). This method has been successful for the modification of a 3,6-dimethoxysilafluorene with PhMgBr. The research involved the synthesis of an array of new germafluorenes by the reaction sequence presented in FIG. 12 utilizing a range of alkynyl-based substituents to introduce functional groups at the 2,7-positions for the preparation of 19c-g. The alkynyl-based reagents that were investigated are either commercially available or readily prepared by literature procedures from the corresponding bromide.

Germa-Rhodamines/Germa-Fluoresceins

In another embodiment of the present disclosure, the compounds are substituted germa-fluoresceins or germa-rhodamines having the general formula (III)

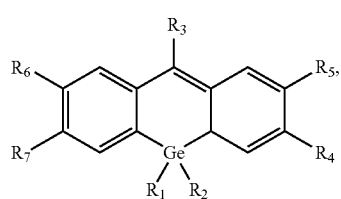
(III)

wherein $R_1$ and $R_2$ may be independently selected from the group consisting of aryl, alkyl, halide, alkynyl, and asymmetric derivatives thereof with two different groups at the Ge-center;
wherein $R_4$ and $R_7$ may be independently selected from the group consisting of =O, —OH, and $OSi(CH_3)_2[C(CH_3)_3]$ hydroxyl or carbonyl amine and ether derivatives;
wherein $R_5$ and $R_6$ are H; and,
wherein $R_3$ is Y, =O, $C_6H_5$, p-$CH_3C_6H_5$, p-$CH_3OC_6H_5$ or

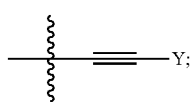

wherein Y is

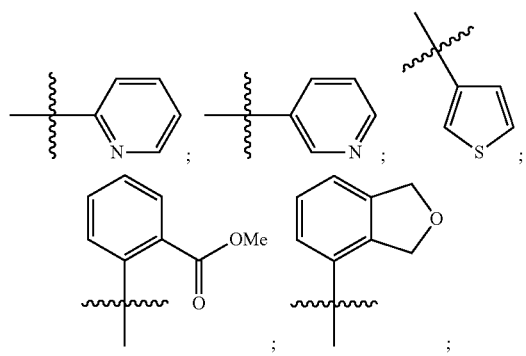

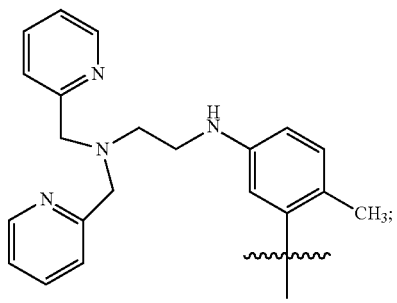

wherein Z is F, $CH_3$ or $OCH_3$:

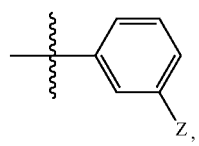

wherein X=$CF_3$, OPh, $CH_3$, Ph, $OCH_3$ or $OCF_3$:

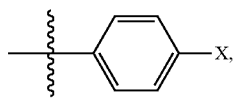

wherein $NR_2$=$NH_2$, $NMe_2$, or $NEt_2$ and Z=Me, $CO_2H$, C(=O)H, or $CO_2Me$;

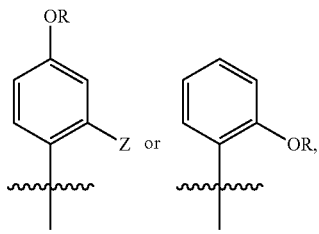

wherein R is alkyl and Z=Me, $CO_2H$, C(=O)H, or $CO_2Me$; or,

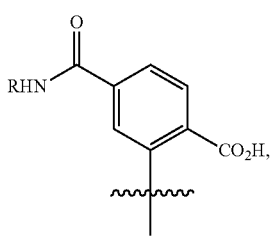

wherein R is alkyl or H.

Figure 16:
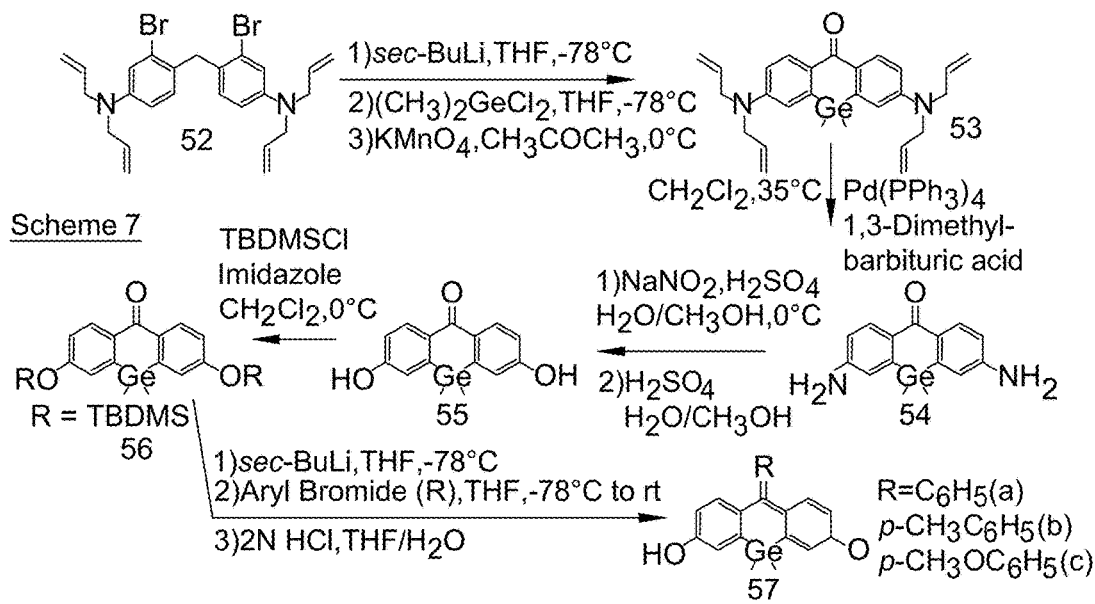
FIG. 16 illustrates an exemplary synthesis scheme for germa-fluorescein and germa-rhodamine compounds of the present disclosure.

FIG. 16 illustrates an exemplary synthesis for germafluoresceins and germa-rhodamines. In one aspect of the present disclosure, formula (III) includes germaanthracenes. Germaanthracene analogs are highly conjugated and have a six-membered planar ring at the core of the molecule.

The anthracene motif has been successfully used as the core of several well known and highly fluorescent molecules such as fluorescein and rhodamine which have been invaluable to biological research applications as labels and sensors for biomolecules, probes for various biologically relevant metals and enzymatic activities, and in vivo/in vitro cell imaging. These dyes have many photophysical properties, such as high fluorescent intensity and quantum yields, long excitation and emission wavelengths, and tolerance to photobleaching for the development of red light-emitting Ge-fluorescein derivatives.

Red OLEDs are a vital component of full color displays; however, red-light emitting materials with high electroluminescence abilities and thermal stabilities are more limited in number than blue and green light-emitters. Red-light emitting materials are typically used only as dopants in OLED fabrication which presents multiple problems associated with reliably reproducing the concentration of the doped material for commercial production. Non-doped pure red OLEDS are rare. The difficulty with red light emitting luminophores is that they suffer from aggregation-caused quenching (ACQ) of light emission as they commonly possess one of two characteristics: highly conjugated π-systems or polar donor-acceptor substituents. Either characteristic renders these luminophores prone to crystallization in the solid state which ultimately leads to ACQ and the irreversible loss of fluorescence.

Several Group 14 fluorescein and rhodamine derivatives have been reported whereby the oxygen atom at the ten position of the xanthene moiety has been replaced with silicon or germanium. Two important facts have emerged from these studies. Introduction of silicon or germanium at the ten position within these analogs leads to a significant red shift of the emission and excitation wavelengths which has been attributed to the low-lying LUMO energy levels associated with Group 14 elements. The shift to longer wavelengths has enabled the development of several outstanding, far-red to near infrared fluorescence probes for biological imaging while retaining all of the desirable photophysical properties of fluorescein and rhodamine. Secondly, the fluorescence mechanism in several of the fluorescein analogs can be activated without difficult to control strategies such photoinduced electron transfer (PeT) or spiro-cyclization which are typical in both fluorescein and rhodamine. These studies suggest that is possible to extend the range of fluorescein-based molecules without labor-intensive synthetic strategies. Although no crystal structures of these novel molecules were provided in these studies, it is not unreasonable to assume that the aryl substituent located at position 5 of the xanthene moiety is twisted relative to the xanthene core just as it is in fluorescein. In other words, these fluorescein-based molecules already possess the twisted structure necessary for AIE(E).

In one embodiment of the present disclosure, the compound of formula (III) may have the formula (III-A)

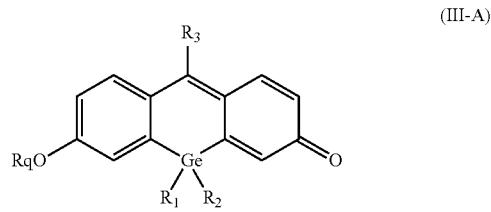

wherein $R_1$ and $R_2$ may be independently selected from the group consisting of aryl, alkyl, halide, alkynyl, and asymmetric derivatives thereof with two different groups at the Ge-center;

wherein $R_3$ is selected from the group consisting of $C_6H_5$, p-$CH_3C_6H_5$, p-$CH_3OC_6H_5$, and another substituted aromatic substituent; and, wherein $R_q$ is H or another substituted aromatic substituent.

Germapins

In yet another embodiment of the present disclosure, the compounds are substituted germapins having the general formula (IV)

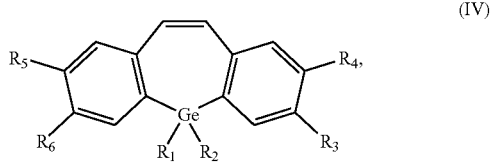

wherein $R_1$ and $R_2$ may be independently selected from the group consisting of aryl, alkyl, halide, alkynyl, and asymmetric derivatives thereof with two different groups at the Ge-center;

wherein $R_3$ and $R_6$ may be independently selected from the group consisting of H, Cl, Ar, Y and

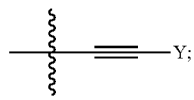

wherein $R_4$ and $R_5$ may be independently selected from the group consisting of H, aryl, I, Br, Y or

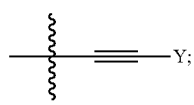

and
wherein Y is

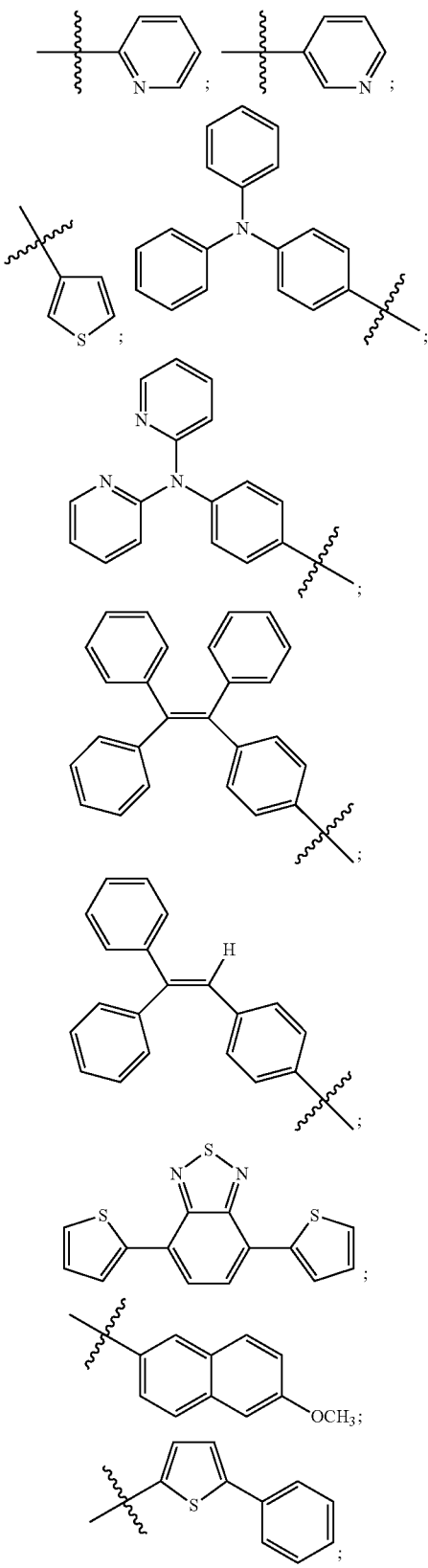

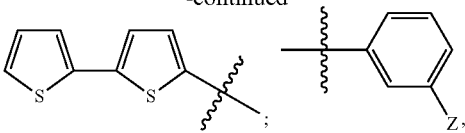

wherein Z is F, CH₃, or OCH₃;

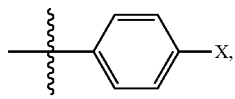

wherein X is CF₃, OPh, CH₃, Ph, OCH₃ or OCF₃; or

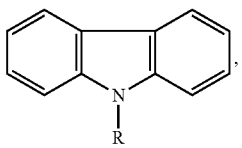

wherein R is aryl, alkenyl or alkynyl.

Figure 17:
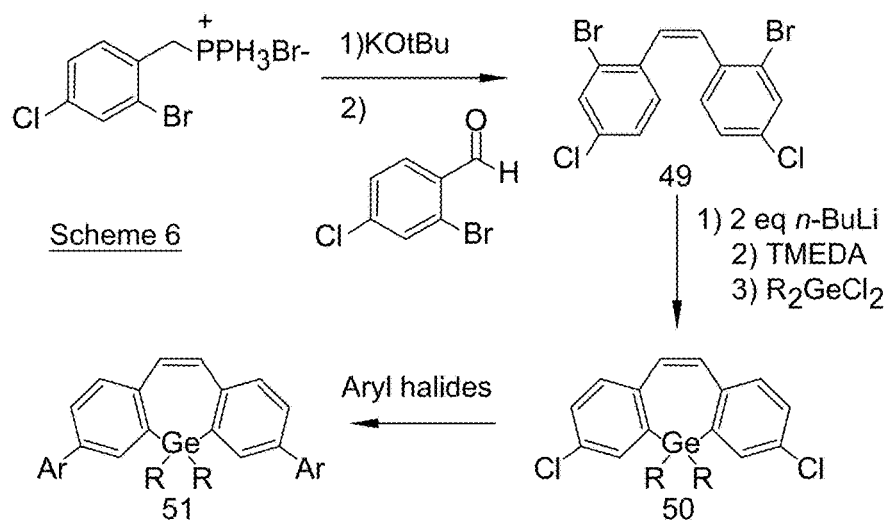
FIG. 17 illustrates an exemplary synthesis scheme for germapin compounds of the present disclosure.

FIG. 17 illustrates an exemplary synthesis for germapins.

The present, disclosure is also directed to the changes that occur in the optical and electrical properties of the molecules disclosed herein as they are modified in size and shape of the central conjugated germanium-containing core. The germapin serves as another unique scaffold for developing strong blue light emitting AIE(E) molecules. Surprisingly, only two germapins have been reported, 5,5-diphenyl- and 5,5-dimethyl-9,10-dihydrido-5H-dibenzo. The crystal structure of the diphenyl derivative exhibited the unique boat conformation that the central seven-membered ring assumes. The silicon analogs, silepins, are air and moisture stable solids which exhibit strong blue fluorescence in solution with quantum yields ranging from 0.40 to 0.93 depending on the site and the type of substitutent incorporated into the conjugated framework.

The synthesis for the germapins is based on a method used by Clegg and coworkers for the preparation of functionalized silapins (shown in Scheme 6, FIG. 17). The stilbene precursor 27 which is key to this method is prepared by a Wittig reaction between a phosphonium aryl salt and a dihalogenated aldehyde in excellent yields and high cis-selectivity. The dichloro-substituted germapin is then obtained by a ring closing reaction between the in situ generated dilithio intermediate and an appropriate dichlorogermane. A variety of substituted derivatives are prepared from the dichloro-germapin 28 which is stable enough to participate in multiple standard cross-coupling reactions such as Suzuki, Stille, and Sonogashira. Initial studies began with Ph₂GeCl₂ and simple aryl bromides such as those described for the preparation of other germanium heterocyles (FIG. 12). The preparation of unsymmetrical germapins is also accomplished by modifying the stilbene precursor which can be done by using a trihalogenated aldehyde in the Wittig reaction.

In one embodiment of the present disclosure, the compound of formula IV may have the formula (IV-A)

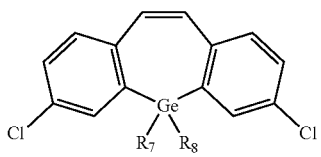

(IV-A)

wherein $R_7$ and $R_8$ may be independently selected from the group consisting of aryl, alkyl, halide, alkynyl, and asymmetric derivatives thereof with two different groups at the Ge-center.

In another embodiment of the present disclosure, the compound of formula IV may also have the formula (IV-B)

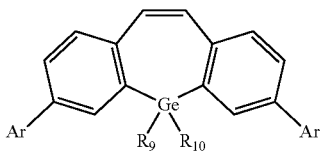

(IV-B)

wherein $R_9$ and $R_{10}$ may be independently selected from the group consisting of aryl, alkyl, halide, alkynyl, and asymmetric derivatives thereof with two different groups at the Ge-center.

EXAMPLES

All reactions of Examples 1-13 were performed under an inert atmosphere of argon using flame or oven dried glassware on a dual-manifold Schlenk line or in a drybox. Diethyl ether and THF were distilled over sodium/9-fluorenone prior to use. Methylene chloride was distilled over $CaH_2$. Chloroform-d was purchased from Cambridge Isotopes Inc., and dried over activated molecular sieves. Other commercially available reagents were purchased from Aldrich Chemical Co. and were used as received. NMR spectra were recorded on Bruker Avance-300 MHz and Bruker ARX-500 MHz instruments at ambient temperature. Spectroscopic data were recorded at 300 MHz and 500 MHz respectively for $^1H$, 125 MHz and 75 MHz respectively for $^{13}C$, 202 MHz for $^{31}P$, and 282 MHz for $^{19}F$. Proton, carbon, phosphorus, and fluorine chemical shifts (δ) are reported relative to the residual protio and deuterio-chloroform, external $H_3PO_4$ and $CFCl_3$, respectively. Chemical shifts are reported in ppm and the coupling constants in hertz. Melting point determinations were obtained on a Mel-Temp melting point apparatus and are uncorrected. UV-vis and fluorescence spectra were measured on a Cary 50 Bio UV-visible and Cary Eclipse Fluorescence spectrophotometer, respectively. Emission spectra were measured using the $\lambda_{max}$ value for each compound as determined by the absorption spectra. Elemental analysis determinations were performed by Atlantic Microlabs, Inc., Norcross, Ga. The X-ray crystallographic data were collected on a Bruker Apex II diffractometer equipped with a CCD area detector.

For solid state PL measurements, aluminum TLC plates (Merck. Silica 60 $F_{254}$) were used. Dichloromethane solutions of the germoles (0.67 mg/ml) were used as the developing media. The coated TLC plates were excited at an angle of 20° in the spectrofluorometer. For dynamic light scattering measurements, the hydrodynamic radius (RH) was measured at room temperature with a DynaPro Titan instrument (Wyatt Technology, Santa Barbara, Calif.). Samples (30 µL) were placed directly into a quartz cuvette, and light scattering intensity was collected at a 90° angle using a 10 s acquisition time. Data regularization with Dynamics (version 6.7.1) generated histograms of percent mass versus RH.

For TEM images, a droplet of 0.05 mM acetone-water mixture was applied to a lacey carbon film on a square mesh copper grid (Ted Pella Inc.) and allowed to air dry at 25° C. The aggregated samples were visualized with a Phillips EM 430 transmission electron microscope operated at 300,000 eV and magnifications of 110,000 and 150,000, respectively.

For SEM images, thin films were prepared by coating quartz slides with ca. $10^{-3}$ M methylene chloride solutions of the germoles. The morphologies were visualized with a JEOL-6320F Field Emission scanning electron microscope (SEM) after sputtering a thin layer of gold onto the samples with a Hummer VI sputtering system. The operating parameters for the images were taken with the lower detector were: an acceleration voltage of 5 keV, probe current #3, objective lens aperture 3, and a working distance of 15 mm. The operating parameters for higher detector were similar except that an acceleration voltage of 15 keV and a working distance of 8 mm were employed.

Example 1

Formation of 1,1'-Bis(4-(trifluoromethyl)phenyl)-2,3,4,5-tetraphenylgermole (2)

A solution of n-BuLi (0.50 mL, 2.5 M in hexane, 1.3 mmol) was added dropwise to a solution of 1-ethynyl-4-trifluorotoluene (0.20 mL, 1.3 mmol) in dry THF (1.5 mL) that had been cooled to −78° C. Once the addition was complete, the colorless reaction mixture was stirred at this temperature for 15 minutes. The resulting alkynyllithium solution was then added in one portion to a solution of 1,1'-dichloro-2,3,4,5-tetraphenylgermole (0.31 g, 0.63 mmol) in dry THF (5 mL) that had been cooled to 0° C. The yellow reaction mixture was allowed to gradually warm to room temperature and stirred overnight. The reaction mixture was quenched with water (0.25 mL), stirred for an additional 15 minutes, and then dried over $MgSO_4$. After filtering, the solvent was removed by rotary evaporation. The crude product was purified on a silica gel column using a toluene/hexane (2:1) as the eluent to give 2 as a yellow solid (340 mg, 71%). X-ray quality crystals were grown by slow evaporation from a methylene chloride/diethyl ether mixed solvent system. All of the other germoles were prepared in a similar manner. The eluent and recrystallization solvent systems used in the purification of each germole are indicated.

Example 2

Formation of 1,1-Bis(4-(trifluoromethyl)phenyl)-2,3,4,5-tetraphenylgermole (2)

M.p. 179-180° C. $^1HNMR$ (500 MHz): δ 7.63 (d, J=8 Hz, 4H), 7.57 (d, J=8 Hz, 4H), 7.22 (d, J=8 Hz, 4H), 7.16 (t, J=8 Hz, 4H), 7.14-7.09 (m, 2H), 7.09-7.03 (m, 6H), 6.91-6.86 (m, 4H). $^{13}C\{^1H\}$ NMR (125 MHz): δ 153.5, 138.4, 137.7, 135.4, 132.7, 130.9 (q, J=33 Hz), 129.85, 129.80, 128.2, 127.9, 127.0, 126.9, 126.2, 125.3 (q, J=8 Hz), 124.9, 105.8, 88.6. $^{19}F\{^1H\}$ NMR (282 MHz): δ −62.9. Anal. Calcd. for $C_{46}H_{28}F_6Ge$: C, 72.00; H, 3.68. Found: C, 71.74; H, 3.57.

Example 3

Formation of 1,1-Bis(4-(trifluoromethoxy)phenyl)-2,3,4,5-tetraphenylgermole (3)

Purification of (3) by column chromatography using silica gel and toluene/hexane (2:1) as the eluent yielded a yellow solid (461 mg, 67%). (M.p. 113-114° C. $^1$H NMR (500 MHz): δ 7.61-7.57 (m, 4H), 7.28-7.25 (m, 4H), 7.22-7.17 (m, 8H), 7.17-7.14 (m, J=5, 2 Hz, 2H), 7.13-7.07 (m, 6H), 6.94-6.90 (m, 4H). $^{13}$C{$^1$H} NMR (125 MHz): δ 153.4, 149.6, 138.6, 137.8, 135.8, 134.1, 129.9, 129.8, 128.2, 127.9, 126.9, 126.8, 121.3, 120.9, 119.5, 105.8, 86.9. $^{19}$F{$^1$H} NMR (282 MHz): δ −57.7. Anal. Calcd. For $C_{46}H_{28}F_6GeO_2$: C, 69.12; H, 3.53. Found: C, 68.71; H, 3.59.

Example 4

Formation of 1,1-Bis(p-tolyltheynyl)-2,3,4,5-tetraphenylgermole (4)

Purification of (4) by column chromatography using silica gel and hexane/toluene (2:1) as the eluent yielded a yellow solid (317 mg, 70%). Yellow crystals were grown by slow evaporation from a methylene chloride/hexane mixed solvent system. M.p. 210.5-212° C. $^1$H NMR (CDCl$_3$): δ 7.45 (d, J=8 Hz, 4H), 7.31-7.27 (m, 5H), 7.20-7.12 (m, 10H), 7.11-7.05 (m, 6H), 6.94-6.90 (m, 4H), 2.38 (s, 6H). $^{13}$C{$^1$H} NMR (125 MHz): δ 152.9, 139.4, 138.8, 138.1, 136.4, 132.4, 130.0, 129.8, 129.1, 128.1, 127.8, 126.7, 126.6, 119.6, 107.5, 85.2, 21.7. Anal. Calcd. for $C_{46}H_{34}Ge$: C, 83.79; H, 5.20. Found: C, 83.46; H, 5.64.

Example 5

Formation of 1,1-Bis((4-methoxyphenyl)ethynyl)-2,3,4,5-tetraphenylgermole (5)

Purification of (5) by column chromatography using silica gel and toluene/hexane (2:1) as the eluent yielded a yellow solid (200 mg, 46%). Yellow crystals were grown by slow evaporation from a tetrahydrofuran/methanol mixed solvent system. M.p. 250-252° C. $^1$H NMR (500 MHz): δ 7.48-7.43 (m, 4H), 7.24 (m, 4H), 7.14 (m, 4H), 7.11-7.06 (m, 2H), 7.06-7.01 (m, 6H), 6.90-6.86 (m, 4H), 6.84-6.80 (m, 4H), 3.79 (s, 6H). $^{13}$C{$^1$H} NMR (125 MHz): δ 160.3, 152.8, 138.9, 138.2, 136.5, 134.0, 129.9, 129.8, 128.1, 127.8, 126.7, 126.5, 114.8, 113.9, 107.3, 84.4, 68.1, 55.4, 25.7. Anal. Calcd. for $C_{46}H_{34}GeO_2$. 1 $C_4H_8O$: C, 78.65; H, 5.54. Found: C, 78.45; H, 5.42.

Example 6

Formation of 1,1-Bis((1,1-biphenyl)-4-ylethynyl)-2,3,4,5-tetraphenylgermole (6)

Purification of (6) by column chromatography using silica gel and hexane/toluene (2:1) as the eluent yielded a yellow solid (282 mg, 58%). Yellow crystals were grown by slow evaporation from a tetrahydrofuran/methanol mixed solvent system. M.p. 186-188° C. $^1$H NMR (500 MHz): δ 7.63-7.53 (m, 12H), 7.47-7.41 (m, 4H), 7.38-7.34 (m, 2H), 7.29-7.27 (m, 4H), 7.19-7.14 (m, 4H), 7.13-7.09 (m, 2H), 7.08-7.03 (m, 6H), 6.93-6.87 (m, 4H). $^{13}$C{$^1$H} NMR (125 MHz): δ 153.1, 141.9, 140.4, 138.8, 138.0, 136.2, 132.9, 129.98, 129.87, 129.0, 128.2, 127.92, 127.88, 127.2, 127.0, 126.8, 126.7, 121.5, 107.2, 86.7. Anal. Calcd. for $C_{56}H_{38}Ge$: C, 85.84; H, 4.89. Found: C, 85.86; H, 4.82.

Example 7

Formation of 1,1-Bis((4-phenoxyphenyl)ethynyl)-2,3,4,5-tetraphenylgermole (7)

Purification of (7) by column chromatography using silica gel and hexane/toluene (2:1) as the eluent yielded a yellow solid (254 mg, 50%). Yellow crystals were grown by slow evaporation from a tetrahydrofuran/methanol mixed solvent system. M.p. 204-205° C. $^1$H NMR (500 MHz): δ 7.54-7.49 (m, 4H), 7.42-7.36 (m, 4H), 7.30-7.25 (m, 4H), 720-7.15 (m, 6H), 7.14-7.10 (m, 2H), 7.10-7.07 (m, 6H), 7.06-7.02 (m, 4H), 6.96-6.92 (m, 4H), 6.92-6.89 (m, 4H). $^{13}$C{$^1$H} NMR (125 MHz): δ 158.4, 156.4, 153.0, 138.8, 138.1, 136.3, 134.2, 130.1, 130.0, 129.8, 128.1, 127.9, 126.8, 126.6, 124.1, 119.7, 118.2, 117.1, 106.9, 85.2. Anal, Calcd. for $C_{56}H_{38}GeO_2$: C, 82.47; H, 4.70. Found: C, 82.16; H, 4.82.

Example 8

Formation of 1,1-Bis((3-fluorophenyl)ethynyl)-2,3,4,5-tetraphenylgermole (8)

Purification of (8) by column chromatography using silica gel and hexane/toluene (2:1) as the eluent yielded a yellow solid (271 mg, 65%). Yellow crystals were grown by slow evaporation from a methylene chloride/hexane mixed solvent system. M.p. 181.5-182.5° C. $^1$H NMR (500 MHz): δ 7.32-7.28 (m, 4H), 7.22 (m, 6H), 7.16 (m, 4H), 7.13-7.09 (m, 2H), 7.08-7.03 (m, 8H), 6.90-6.86 (m, 4H). $^{13}$C{$^1$H} NMR (125 MHz): δ 162.4 (d, J=247 Hz), 153.3, 138.6, 137.8, 135.7, 130.0 (d, J=9 Hz), 129.9, 129.8, 128.3 (d, J=3 Hz), 128.2, 127.9, 126.9, 126.8, 124.3 (d, J=9 Hz), 119.2 (d, J=23 Hz), 116.7 (d, J=22 Hz), 105.9 (d, J=3 Hz), 86.9. $^{19}$F{$^1$H} NMR (282 MHz): δ −113.2. Anal. Calcd. for $C_{44}H_{28}F_2Ge$: C, 79.19; H, 4.23. Found: C, 78.83; H, 4.00.

Example 9

Formation of 1,1-Bis(thiophen-3-ylethynyl)-2,3,4,5-tetraphenylgermole (9)

Purification of (9) by column chromatography using silica gel and hexane/toluene (2:1) as the eluent yielded a yellow solid (418 mg, 70%). Yellow crystals were grown by slow evaporation from a methylene chloride/hexane mixed solvent system. M.p. 254-255.5° C. $^1$H NMR (500 MHz): δ 7.60 (d, J=3 Hz, 2H), 7.28-7.24 (m, 6H), 7.22-7.14 (m, 6H), 7.14-7.10 (m, 2H), 7.10-7.05 (m, 6H), 6.93-6.88 (m, 4H). $^{13}$C{$^1$H} NMR (125 MHz): δ 153.1, 138.8, 138.0, 136.1, 130.9, 130.4, 130.0, 129.9, 128.1, 127.9, 126.8, 126.7, 125.4, 121.9, 102.3, 85.6. Anal. Calcd. for $C_{40}H_{26}GeS_2$: C, 74.67; H, 4.07. Found: C, 74.88; H, 3.97.

Example 10

Formation of 1,1-Bis((3-pyridinyl)ethynyl)-2,3,4,5-tetraphenylgermole (10)

Purification of (10) by column chromatography using silica gel and methanol as the eluent yielded a yellow solid (472 mg, 60%). Yellow crystals were grown by slow evaporation from a methylene chloride/diethyl ether mixed solvent system. M.p. 220-221.5° C. $^1$H NMR (300 MHz): δ 8.76

(dd, J=2, 0.7 Hz, 2H), 8.56 (dd, J=5, 1.7 Hz, 2H), 7.81 (dt, J=8, 1.9 Hz, 2H), 7.29-7.03 (m, 16H), 6.91-6.86 (m, 4H). $^{13}C\{^1H\}$ NMR (125 MHz): δ' 153.5, 153.1, 149.5, 139.3, 138.5, 137.7, 135.5, 129.9, 129.8, 128.3, 128.0, 127.0, 126.9, 123.1, 119.7, 104.0, 89.7. Anal. Calcd. for $C_{42}H_{28}GeN_2$: C, 79.65; H, 4.46. Found: C, 79.18; H, 4.36.

Example 11

Formation of 1,1-Bis((2-pyridinyl)ethynyl)-2,3,4,5-tetraphenylgermole (11)

Purification of (11) by column chromatography using silica gel and methanol as the eluent yielded a yellow solid (447 mg, 66%). Yellow crystals were grown by slow diffusion from a hexane/methylene chloride (2:1) mixed solvent system. M.p. 260° C. (dec.). $^1H$ NMR (300 MHz): δ 8.59 (ddd, J=4.9, 1.7, 0.9 Hz, 2H), 7.66 (td, J=7.7, 1.8 Hz, 2H), 7.54 (dt, J=7.8, 1.1 Hz, 2H), 7.29-7.19 (m, 6H), 7.15-7.02 (m, 10H), 6.90-6.84 (m, 4H). $^{13}C\{^1H\}$ NMR (75 MHz): δ 153.8, 150.4, 142.9, 138.9, 137.9, 136.6, 135.7, 130.2, 130.2, 128.5, 128.4, 128.2, 127.1, 127.0, 124.0, 105.9, 86.6. Anal. Calcd. for $C_{42}H_{28}GeN_2$: C, 79.65; H, 4.46. Found: C, 79.39: H, 4.91.

Example 12

Formation of 1,1-Bis((diphenylphosphino)ethynyl)-2,3,4,5-tetraphenylgermole (12)

Purification of (12) by column chromatography using silica gel and hexane/toluene (2:1) as the eluent yielded a yellow solid (450 mg, 44%). Yellow crystals were grown by slow evaporation from diethyl ether. p. 154.5-156° C. $^1H$ NMR (500 MHz): δ 7.58-7.53 (m, 8H), 734-7.24 (m, 14H), 7.23-7.19 (m, 4H), 7.16-7.13 (m, 6H), 7.10-7.05 (m, 6H), 6.89 (dd, J=8, 1.7 Hz, 4H). $^{13}C\{^1H\}$ NMR (125 MHz): δ 153.4, 138.5, 137.6, 135.7, 135.5 (d, $J_{PC}$=6 Hz), 132.7 (d, $J_{PC}$=21 Hz), 130.0, 129.9, 129.2, 128.8 (d, $J_{PC}$=8 Hz), 128.2, 127.9, 126.9, 126.8, 107.2 (d, $J_{PC}$=18 Hz), 106.5 (d, $J_{PC}$=3 Hz). $^{31}P\{^1H\}$ NMR (202 MHz): δ −32.2. Anal. Calcd. for $C_{56}H_{40}GeP_2$: C, 79.36; H, 4.76. Found: C, 79.69; H, 5.06.

Example 13

X-Ray Structure Determination.

Crystals of x-ray diffraction quality were obtained by slow evaporation from a methylene chloride/hexane mixed solvent system for 8 and a slow evaporation of a saturated diethyl ether solution for 12. Crystals of appropriate dimension were mounted on a glass capillary in a random orientation. Preliminary examination and data collection were performed using a Bruker Kappa Apex II Charge Coupled Device (CCD) Detector system single crystal X-Ray diffractometer using an Oxford Cryostream LT device. Data were collected using graphite monochromated Mo Kα radiation (λ=0.71073 Å) from a fine focus sealed-tube X-Ray source. Preliminary unit cell constants were evaluated with a set of 36 narrow frame scans. Typical data sets consist of combinations of ω̄ scan frames with typical scan width of 0.5° and exposure time of 15-20 seconds/frame at a crystal to detector distance of 4.0 cm. The collected frames were integrated using an orientation matrix determined from the narrow frame scans. Apex II and SAINT software packages were used for data collection and data integration. Final cell constants were determined by global refinement of reflections from the complete data set. Collected data were corrected for systematic errors using SADABS based on the Laue symmetry using equivalent reflections.

Structure solution for 8 was carried out using the SIR-92 software package, and structure refinement was performed using the CRYSTALS software package. Structure solution and refinement for 12 was performed using the SHEL-XTL 97 package. The structures were solved by direct methods in the triclinic space group P1̄ and refined with full matrix least-squares refinement by minimizing $\Sigma w(F_o^2 - F_c^2)^2$. All non-hydrogen atoms were refined anisotropically to convergence. One of the phenyl rings in 12 is disordered over two positions. Disorder was resolved with 50% occupancy atoms. All H atoms were added in the calculated position and were refined using appropriate riding models. The models were refined to convergence to the final residual values of $R_1$=4.0% and $wR_2$=11.2% for 8, and $R_1$=3.9% and $wR_2$=13.1% for 12.

Example 14

Preparation of unsymmetrical 1,1'-substituted germoles from 1-chloro-1-ethynyl-2,3,4,5-tetraphenylgermole For the unsymmetrical 1,1'-substituted germoles, the Curtis procedure was used to prepare a 1-chloro-1,2,3,4,5-pentaphenylgermole precursor (13). Reaction of this precursor (13) with the Grignard reagent, ethynylmagnesium bromide, afforded a 1-ethynyl-1,2,3,4,5-pentaphenylgermole (14) (Scheme 2-3).

Scheme 2-3: Prepaartion of the building block for unsymmetrical germoles

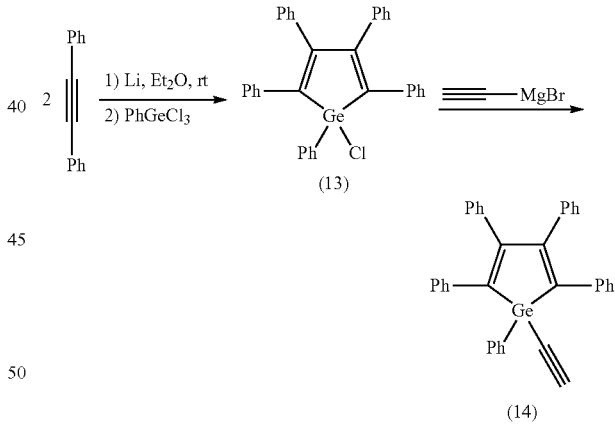

It was anticipated that the 1-ethynyl-1,2,3,4,5-pentaphenylgermole (14) would be stable enough to undergo a conventional palladium-catalyzed cross-coupling reaction. Reactions between terminal alkynes and aryl iodides appear to be quite tolerant of polar functional groups such as amines, hydroxyls, and esters. Such groups are extremely difficult to introduce by any other synthetic means but are highly desirable for sensory applications and biological probe applications for which similar siloles have been used. Unsymmetrical 1,1'-substituted germoles are expected to exhibit significantly higher quantum efficiencies in the solid state than their symmetrical analogs. Related siloles differing in 1,1'-substitution exhibited higher solid state quantum efficiencies compared to the symmetrical 1,1-substituted siloes which was attributed to a higher degree of difficulty in packing compactly in the solid state.

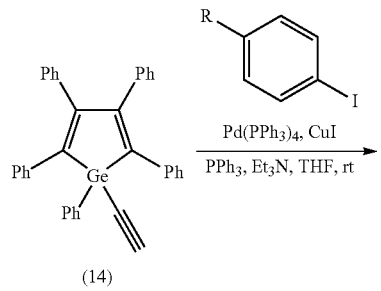

(14)

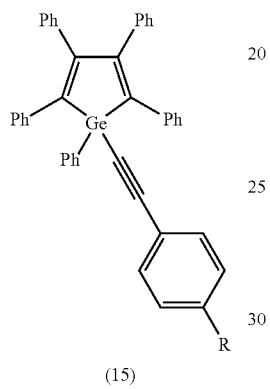

(15)

Example 15

Preparation of 2,7- and 3,6-Disubstituted Germafluorenes

Germafluorenes were investigated to gain insight into changes of the optical and electrical properties upon expanding the germole core. Group 14 fluorenes such as sila- and germafluorene were of particular interest as they are increasingly being used as key building blocks in conjugated polymers. The optical and electronic properties of these π-conjugated materials are intricately tied to their electronic structures which can be tuned by incorporating functional groups, fused aromatic rings, and bridging heteroatoms. In an effort to improve upon these materials, synthetic methods for the preparation of germafluorenes with broad structural variations that satisfy requirements for conjugation control need to be developed. The current limited numbers of studies using germafluorenes have illustrated the promise of these heterocycles for electronic applications; thus, further investigations of the properties of various germafluorenes were required for the development of advanced materials.

Many of the structural prerequisites for AIE(E) molecules can be readily incorporated into germfluorenes at several of the sites of substitution to minimize the problems associated with the aggregation that is notorious for rendering luminophors ineffective for solid state applications in electroluminescent devices. The fluorene central core provides three sites for substitution that would allow structure-property investigations: the exocyclic positions (9,9=R) directly attached to the germanium as well as those meta (2,7=R1) and para (3,6=R2) to the germanium center.

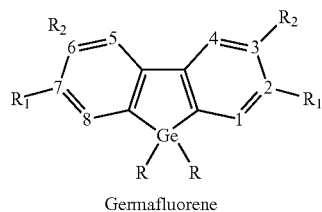

Germafluorene

Reported herein is the preparation of a series of 2,7- and 3,6-disubstituted germafluorenes. This example relates to the synthetic methods used to prepare the different dihalo precursors and functionalized monomers.

A 2,7-dibromo-3,6-dimethoxy-9,9-germafluorenes building block was initially selected as it was thought that this heterocycle would broadened the scope of 2,7-functionalized monomers. Not only does the methoxy substituent serve as an ortho/para directing, group as well as a NMR marker, but it serves as a site for substitution to extend the π-conjugated system of the germafluorene. Using a nickel catalyzed cross-coupling reaction with phenylmagnesium bromide, under conditions referred to as Dankwardt's conditions, the methoxy substituent can be replaced by a phenyl ring.

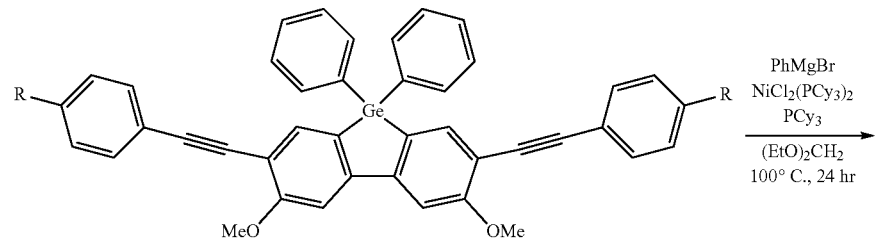

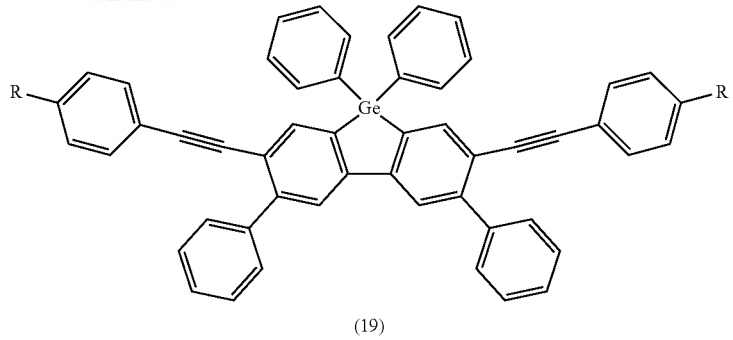

(19)

The preparation of the 2,7-dibromo-3,6-dimethoxy-9,9-germafluorene (16) was accomplished through three separate reactions by utilizing a modified procedure originally published by Huang. The formation of the tetrahalobiphenyl was crucial to the overall success of this route since 9-heterofluorenes cannot withstand typical brominating or iodinating methods and are prone to cleavage; therefore, it was necessary to halogenate the biphenyl prior to the ring closing step. The starting material, o-dianisidine, was commercially available and underwent a diazotization reaction followed by a modified Sandmeyer reaction to yield the 4,4-dibromo-3,3-dimethoxybiphenyl. The 4,4-dibromo-3,3-dimethoxybiphenyl was then iodinated using an iodine/Potassium iodate system to yield the 6,6-diiodo-4,4-dibromo-3,3-dimethoxybiphenyl. Using the reactivity difference of iodo and bromo substituents towards n-butyllithium, the iodo substituents selectively underwent a halogen/metal exchange reaction followed by ring closure with a germanium reagent, dichlorodiphenylgermane. Simple aryl substituents such as phenyls were initially selected as the substituents at the 9,9-positions because they provide the steric congestion necessary to disrupt the packing arrangement of AIE(E) molecules and should aid the thermal stability of the molecules by increasing the melting points.

The preparation of a 3,6-dibromo-9,9-germafluorene (20) was accomplished through four separate reactions by utilizing a modified procedure originally published by Holmes. Like the earlier synthetic pathway for the 2,7-dibromo-3,6-dimethoxy-9,9-germafluorene (16), it was necessary to construct the tetrahalobiphenyl precursor prior to the formation of the germafluorene. However, in this case, a suitable biphenyl was not commercially available and had to be prepared. The commercially available 1,2-dibromo benzene was selected as the starting reagent as it could be coupled to yield 2,2'-dibromobiphenyl which would serve as the organic framework for the heterocycle but required conversion to the 2,2'-diiodo analog. A second halogen/metal exchange reaction of 2,2'-dibromobiphenyl followed by quenching with iodine gave the requisite 2,2'-diiodobiphenyl that then was then brominated utilizing, an iron catalyst to yield the key tetrahalobiphenyl precursor. This particular route of substitution was necessary in order to obtain the biphenyl with the iodo substituents in the 2,2'-positions so that a selective halogen metal exchange between the iodo substituents and n-butyllithium would yield the ring closed product, 3,6-dibromo-9,9-dibenzogermafluorene (20).

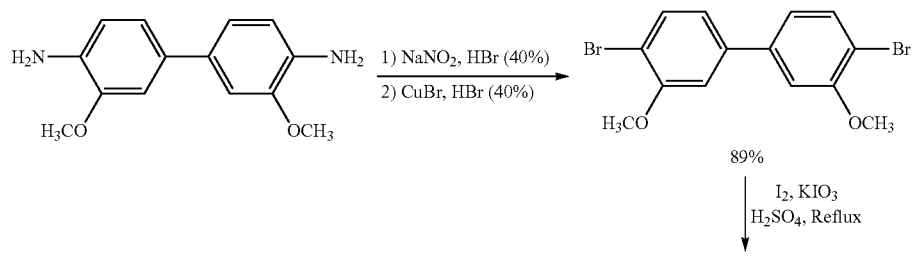

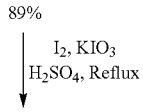

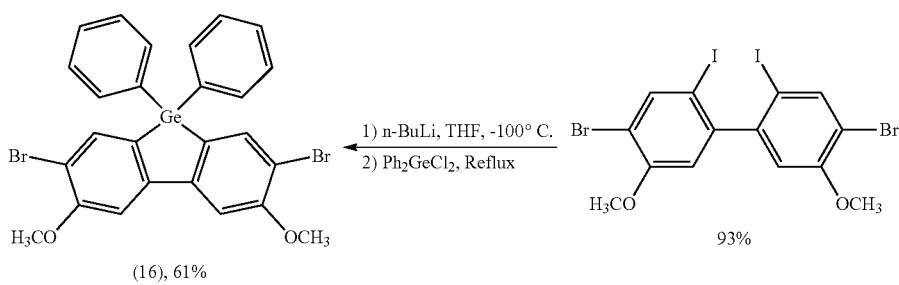

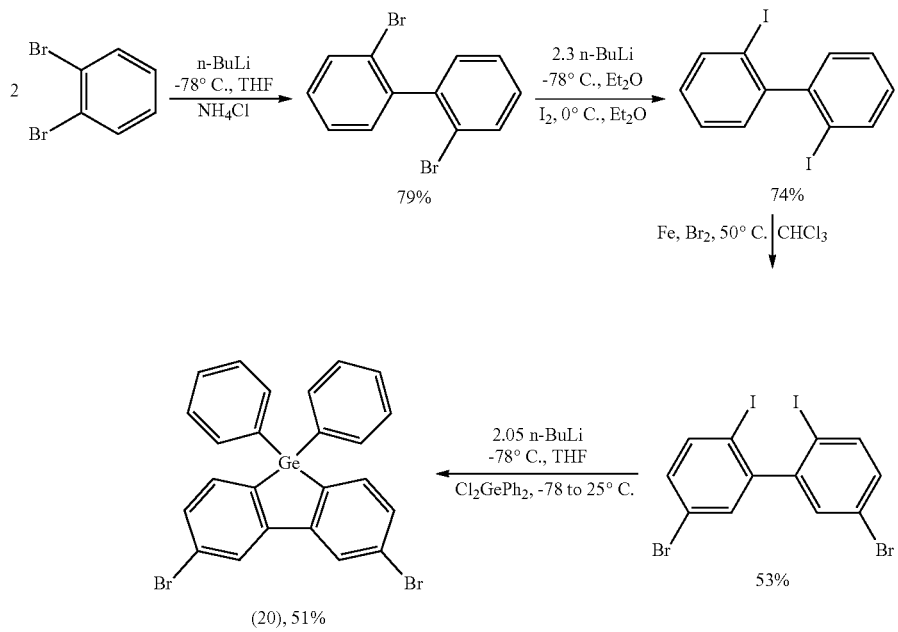

Synthetic procedures were also developed that allowed covalent decoration of discrete germafluorene monomers with a variety of substituents that were anticipated to exhibit high efficiency luminescence particularly in the solid state. Although processes such as donor-acceptor push-pull interactions, J-aggregate formation, or twisted intramolecular charge transfer (TICT) between polar functional groups do not activate the AIE(E) effect, incorporation of functional groups may allow control of the emission color. Therefore, a series of substituents was selected, which were known to exhibit a particular emission wavelength in siloles, for incorporation into the 2,7-dibromo-3,6-dimethoxy-9,9-germafluorene (16) and 3,6-dibromo-9,9-germafluorene (20). The 4-ethynyl-trifluorotoluene was purchased commercially while the other three substituents, 4-(ethynylphenyl)diphenylaniline), 9-(4-bromophenyl)-9H-carbazole, and 2-(4-bromobenzylidene)malononitrile, were prepared according to known literature procedures. It was anticipated that these discrete monomers may perform as well or better than their polymeric counterparts,

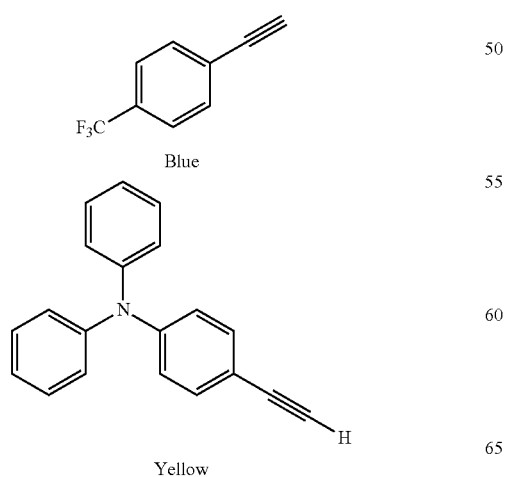

Blue

Yellow

-continued

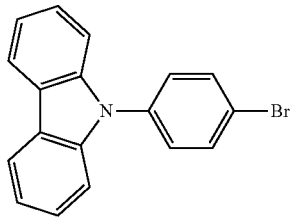

Green

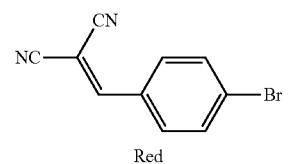

Red

These substituents were incorporated into the dihalo precursors using classical Sonogashira cross-coupling reactions. The 2,7-dibromo-3,6-dimethoxy-9,9-germafluorene (16) or 3,6-dibromo-9,9-germafluorene (20) were coupled to the prepared terminal alkynes (4-ethynyl-trifluorotoluene and 4-(ethynylphenyl)diphenylaniline in an amine and THF mixed solvent with tetrakis(triphenylphosphine)palladium (0) and copper(I) iodide as co-catalysts. Therefore, in hopes of improving the efficiencies of these reactions, the bromo substituents were replaced by an ethynyl linkage such that the coupling could now result in the coupling of a carbon-carbon bond instead of a carbon-bromine bond.

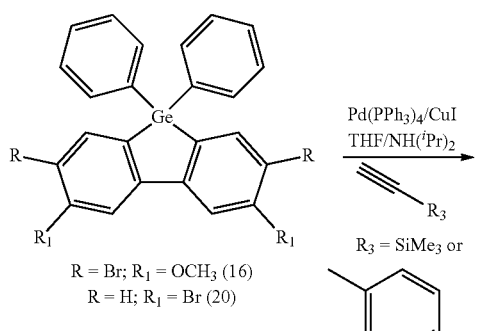

R = Br; R₁ = OCH₃ (16)
R = H; R₁ = Br (20)

Pd(PPh₃)₄/CuI
THF/NH(ⁱPr)₂

R₃ = SiMe₃ or

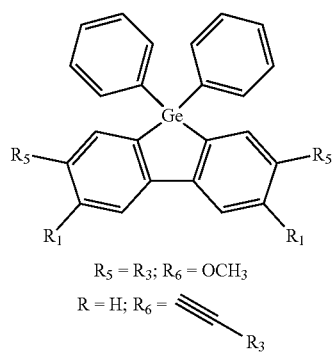

R₅ = R₃; R₆ = OCH₃
R = H; R₆ =

Example 16

Preparation of Fluorescein-Based Molecules Containing Germanium.

This class of heterocycles was prepared using modifications of a procedure which was originally developed for silicon. The entire synthetic pathway required the sequential preparation of six precursor compounds in order to obtain the final fluorescein derivative (26) which could potentially serve as the building block for a series of novel germanium heterocycles that are expected to emit in the red region of the electromagnetic spectrum.

In order to synthesize the germaanthrone (22), it was first necessary to prepare the organic framework which would eventually undergo ring closure to obtain the target compound (21). Since none of the precursor compounds for this synthetic pathway were available commercially, this multi-step process began with the protection of 3-bromoaniline with allyl bromide to form the monomer 3-bromo-N,N-diallylaniline. The diallylaniline then underwent an industrial condensation reaction with formaldehyde to yield the diaryl, bis(2-bromo-4-N,N-diallylaminophenyl)methane (21). The diaryl methane (21) represented the completed organic skeleton necessary for ring closure with a substituted germanium dichloride. From this point forward in the synthetic pathway, the substituents on the germaanthrone (22) were manipulated to transform this key compound into the final fluorescein form. The initial manipulation involved a palladium-catalyzed de-allylation reaction to restore the amino groups forming a diamino-germaanthrone (23). The next manipulation is the most important since it is at this point that the germaanthrone (23) is to be converted to the phenol derivative making the final fluorescein-based structure possible.

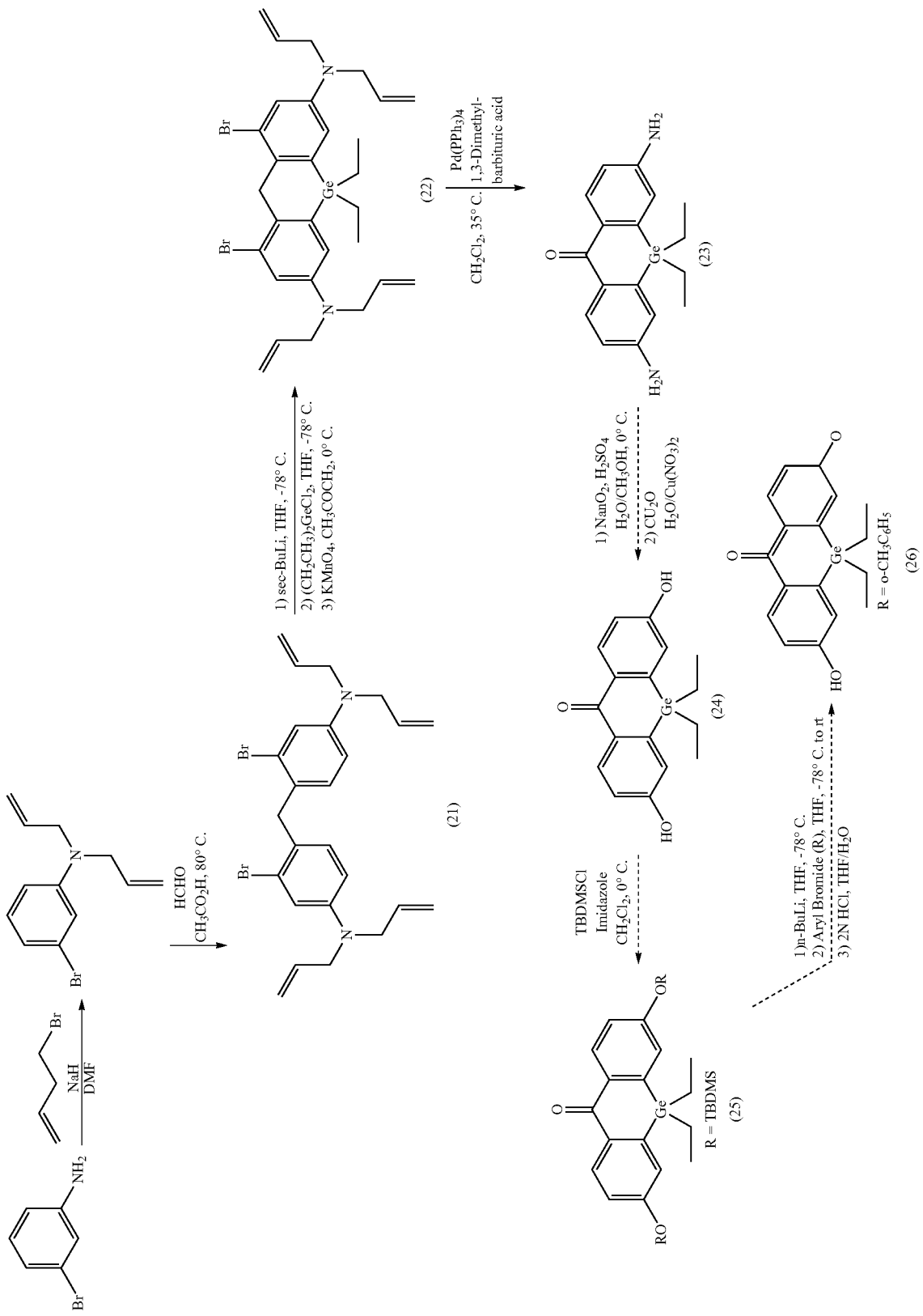

The dihydroxy-germaanthrone (24) can be obtained by conversion to a Tert-butyldimethylsilyl ether (25) with tert-butyldimethylchlorosilane (TBDMS) using imidazole as a catalyst. This process, which may proceed through a N-tert-butyldimethylsilylimidazole intermediate, affords a highly stable protecting group for alcohols. This ether can then be safely coupled with a variety of lithiated aryl substituents at the R position to generate (26). Additionally, the hydroxyl (OH) group on the fluorescein analog (26) can serve as an additional site of substitution to generate other unique derivatives.

While the disclosure has been described in connection with specific embodiments thereof, it will be understood that the inventive device is capable of further modifications. This patent application is intended to cover any variations, uses, or adaptations of the disclosure following, in general, the principles of the disclosure and including such departures from the present disclosure as come within known or customary practice within the art to which the disclosure pertains and as may be applied to the essential features herein before set forth.

What is claimed is:

1. A compound having the formula

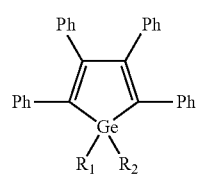
(I)

wherein at least one of $R_1$ and $R_2$ is selected from a substituted aryl or a substituted heteroaryl, and wherein the other one of $R_1$ and $R_2$ may be independently selected from a non-substituted aryl, a substituted aryl, a non-substituted heteroaryl, a substituted heteroaryl, a non-substituted alkynyl, or a substituted alkynyl, and wherein $R_1$ and $R_2$ are different.

2. The compound of claim 1, wherein one of $R_1$ or $R_2$ is a substituted aryl and the other one of $R_1$ or $R_2$ is a non-substituted alkynyl or a substituted alkynyl.

3. The compound of claim 1, wherein $R_1$ and $R_2$ are each

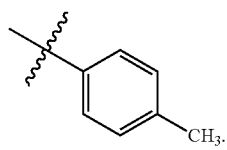 [SMILES: *c1ccc(C)cc1]

4. The compound of claim 1, wherein $R_1$ and $R_2$ are each

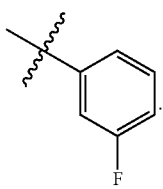 [SMILES: *c1cccc(F)c1]

5. The compound of claim 1, wherein $R_1$ and $R_2$ are each

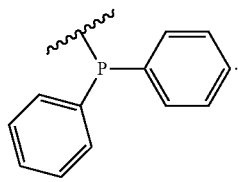 [SMILES: *P(c1ccccc1)c1ccccc1]

6. The compound of claim 1, wherein one of $R_1$ and $R_2$ is

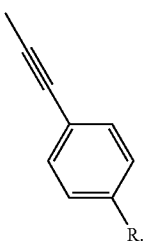

7. The compound of claim 6, wherein R is selected from the group consisting of $CH_3$, $CF_3$, $OCF_3$, $OCH_3$, $N(CH_3)_2$, and $C(CH_3)_3$.

8. The compound of claim 1, wherein the aryl or heteroaryl is selected from the group consisting of

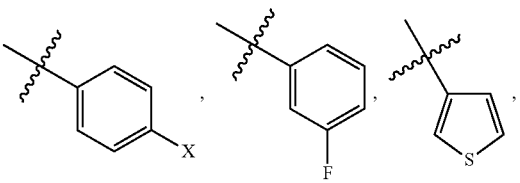

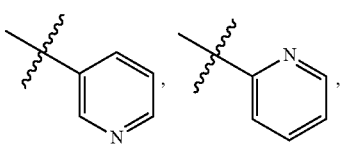

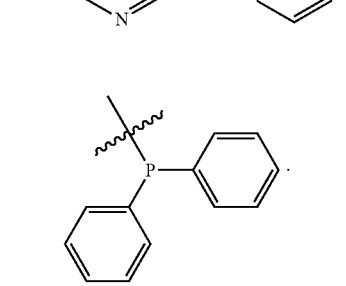

wherein X is selected from the group consisting of H, $CF_3$, $OCF_3$, $CH_3$, $OCH_3$, Ph, OPh and derivatives thereof.

* * * * *